US011145411B2

(12) United States Patent
Treado et al.

(10) Patent No.: US 11,145,411 B2
(45) Date of Patent: Oct. 12, 2021

(54) SYSTEM AND METHOD FOR SERUM BASED CANCER DETECTION

(71) Applicants: CHEMIMAGE CORPORATION, Pittsburgh, PA (US); Patrick Treado, Pittsburgh, PA (US); Shona Stewart, Pittsburgh, PA (US); Heather Kirschner, Moon Township, PA (US); Ryan Priore, Wexford, PA (US); Alan Wilson, Moon Township, PA (US)

(72) Inventors: Patrick Treado, Pittsburgh, PA (US); Shona Stewart, Pittsburgh, PA (US); Heather Kirschner, Moon Township, PA (US); Ryan Priore, Wexford, PA (US); Alan Wilson, Moon Township, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 0 days.

(21) Appl. No.: 14/440,987

(22) PCT Filed: Nov. 6, 2013

(86) PCT No.: PCT/US2013/068671
§ 371 (c)(1),
(2) Date: May 6, 2015

(87) PCT Pub. No.: WO2014/074569
PCT Pub. Date: May 15, 2014

(65) Prior Publication Data
US 2015/0294076 A1    Oct. 15, 2015

Related U.S. Application Data

(60) Provisional application No. 61/765,524, filed on Feb. 15, 2013, provisional application No. 61/848,242, (Continued)

(51) Int. Cl.
*G01N 21/65* (2006.01)
*G01N 33/49* (2006.01)
(Continued)

(52) U.S. Cl.
CPC ............. *G16H 50/20* (2018.01); *G01N 21/65* (2013.01); *G01N 33/49* (2013.01);
(Continued)

(58) Field of Classification Search
None
See application file for complete search history.

(56) References Cited

U.S. PATENT DOCUMENTS 7,060,955 B1    6/2006  Wang
7,990,533 B2 *  8/2011  Maier ................... G01J 3/02
                                                356/301

(Continued)

FOREIGN PATENT DOCUMENTS

JP    2004045390 A    2/2004
JP    2005515423 A    5/2005
(Continued)

OTHER PUBLICATIONS

Extended European Search Report dated Aug. 4, 2016, in corresponding European Application No. 13853852.5.
(Continued)

*Primary Examiner* — Jermele M Hollington
*Assistant Examiner* — Suresh K Rajaputra
(74) *Attorney, Agent, or Firm* — Troutman Pepper Hamilton Sanders LLP

(57) ABSTRACT

A system and method for analyzing biological samples, such as dried human blood serum, to determine a disease state such as colorectal cancer (CRC). Using dried samples may hold potential for enhancing localized concentration and/or segmentation of sample components. The method may com-
(Continued)

prise illuminating at least one location of a biological sample to generate a plurality of interacted photons, collecting the interacted photons and generating at least one Raman data set representative of the biological sample. A system may comprise an illumination source to illuminate at least one location of a biological sample and generate at least one plurality of interacted photons, at least one mirror for directing the interacted photons to a detector. The detector may be configured to generate at least one Raman data set representative of the biological sample. The system and method may utilize a FAST device for multipoint analysis or may be configured to analyze a sample using a line scanning configuration.

50 Claims, 27 Drawing Sheets

Related U.S. Application Data filed on Dec. 28, 2012, provisional application No. 61/797,686, filed on Dec. 13, 2012, provisional application No. 61/796,268, filed on Nov. 6, 2012, provisional application No. 62/089,777, filed on Dec. 9, 2014, provisional application No. 62/113,958, filed on Feb. 9, 2015.

(51) Int. Cl.
    *G16H 50/20*     (2018.01)
    *G16B 40/00*     (2019.01)
    *G01N 33/574*     (2006.01)
    *G01J 3/44*     (2006.01)
    *G01J 3/18*     (2006.01)

(52) U.S. Cl.
    CPC ....... *G01N 33/57419* (2013.01); *G16B 40/00* (2019.02); *G01J 3/1804* (2013.01); *G01J 3/44* (2013.01); *G01J 3/4406* (2013.01)

(56) References Cited

U.S. PATENT DOCUMENTS

| | | | |
|---|---|---|---|
| 8,167,794 B2 | 5/2012 | Matsumoto et al. | |
| 2006/0084876 A1* | 4/2006 | Oh | G01N 21/65 600/476 |
| 2006/0281068 A1* | 12/2006 | Maier | G01N 21/65 435/4 |
| 2008/0117416 A1* | 5/2008 | Hunter | A61B 5/0066 356/301 |
| 2008/0137068 A1* | 6/2008 | Ouchi | G01N 21/3563 356/51 |
| 2008/0151224 A1* | 6/2008 | Treado | G01N 21/65 356/73 |
| 2009/0040519 A1 | 2/2009 | Zhang | |
| 2009/0097020 A1* | 4/2009 | Treado | G01N 21/64 356/301 |
| 2009/0203977 A1* | 8/2009 | Backman | A61B 5/4255 600/325 |
| 2010/0093015 A1 | 4/2010 | Panza et al. | |
| 2012/0083678 A1 | 4/2012 | Drauch et al. | |
| 2012/0200850 A1* | 8/2012 | Stewart | G01N 21/65 356/301 |
| 2013/0176568 A1 | 7/2013 | Priore et al. | |
| 2014/0349337 A1* | 11/2014 | Dasari | G01N 21/65 435/40.5 |
| 2016/0213252 A1 | 7/2016 | Hillman et al. | |

FOREIGN PATENT DOCUMENTS

| | | |
|---|---|---|
| JP | 2006250655 A | 9/2006 |
| JP | 2008552697 A | 7/2008 |
| JP | 2008533448 A | 8/2008 |
| WO | WO2011/088580 A1 | 7/2011 |
| WO | 2014074569 A1 | 5/2014 |

OTHER PUBLICATIONS

Li et al., "Discrimination of serum Raman spectroscopy between normal and colorectal cancer using selected parameters and regression-discriminant analysis," *Applied Optics* (Jul. 20, 2012), Optical Soc. of Amer., Washington DC 5038-5043.

Lin et al., "Colorectal cancer detection by gold nanoparticle based surface-enhanced Raman spectroscopy of blood serum and statistical analysis," *Optics Express* (Jul. 4, 2011) 19(14):13565.

Lloyd et al., "Histological imaging of a human colon polyp sample using Raman spectroscopy and self organising maps," *Vibration. Spectr.* (2013) 60:43-49.

International Search Report and Written Opinion for International Application No. PCT/US2013/068671 dated Feb. 5, 2014.

Okuno et al., Development of multifocal confocal Raman spectroscopy The 4th Molecular Chemistry Panel 2010 lecture abstract (Sep. 14-17, 2010) Osaka, Japan, lecture No. 1B17.

Wang et al., Three-Dimensional Imaging of Ureter With Endoscopic Optical Coherence Tomography, Urology (May 2011), 77(5): 1254-1258.

Sefiane, "On the Formation of Regular Patterns from Drying Droplets and Their Potential Use for Bio-Medical Applications." Journal of Bionic Engineering, vol. 7, 2010, pp. S82-93.

Decision of Rejection for Japanese Patent Application No. 2015-541874 dated Sep. 30, 2019 with English translation.

Dingari et al., "Raman Spectroscopy Provides a Powerful Diagnostic Tool for Accurate Determination of Albumin Glycation," PLOS ONE (Feb. 2012) vol. 7 Issue 2, pp. e32406.

\* cited by examiner

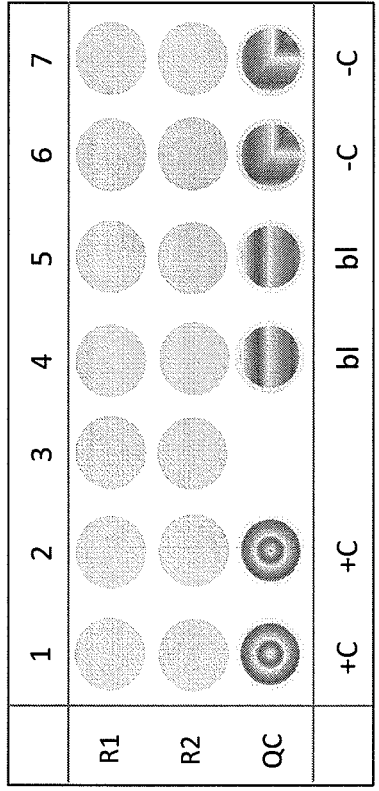
FIG. 7A – Aluminum-coated glass slide (Low Throughput Configuration); 7 patients; 2 duplicates
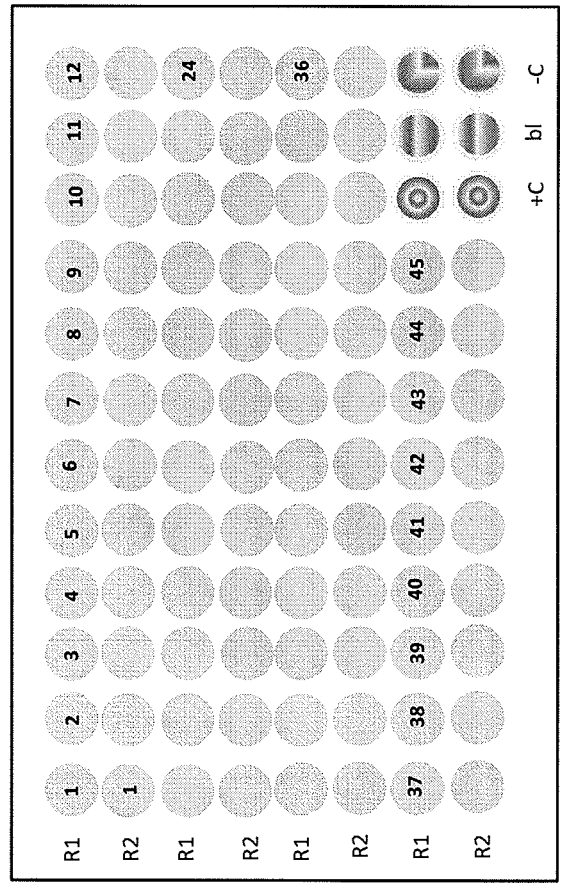
FIG. 7B – 96-Well Plate (High Throughput Configuration) 45 patients; 2 duplicates
Legend
- bl = blank
- +C = positive control
- -C = negative control

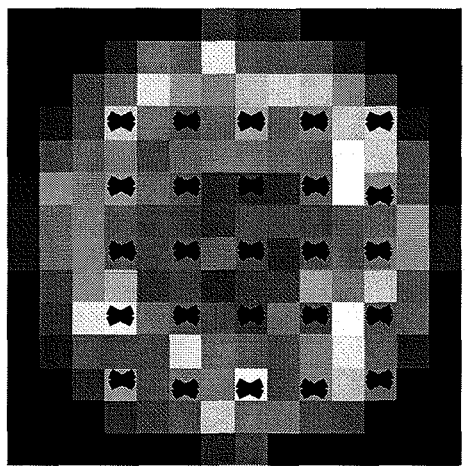
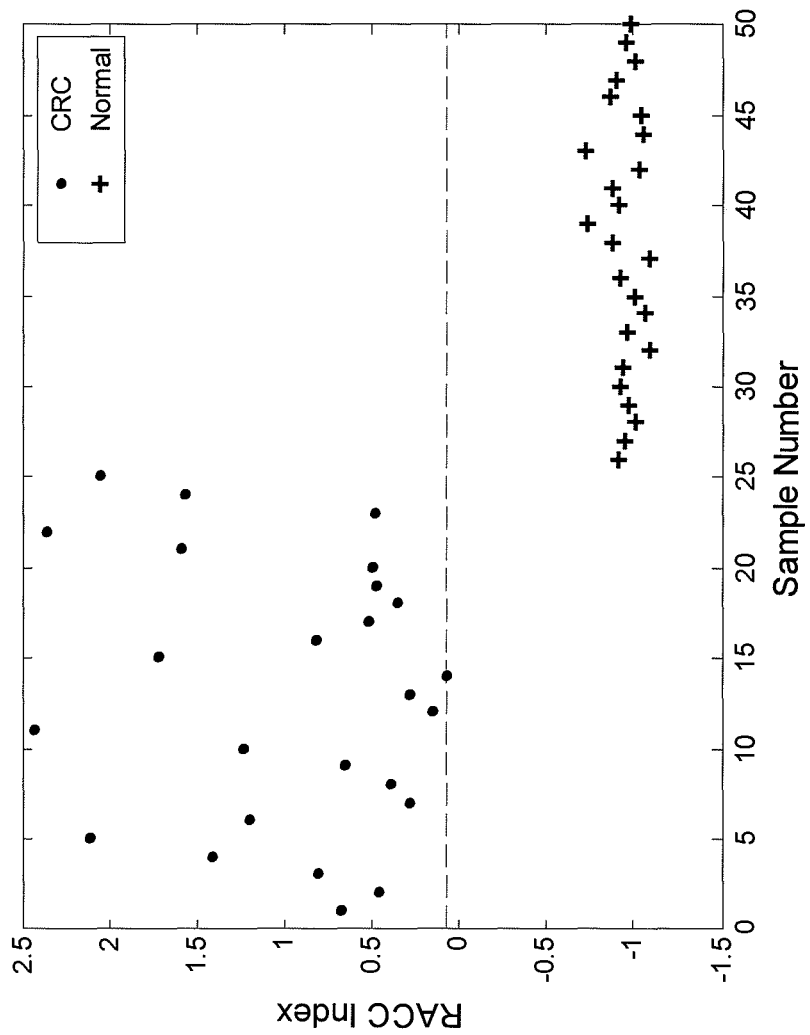
FIG. 12A

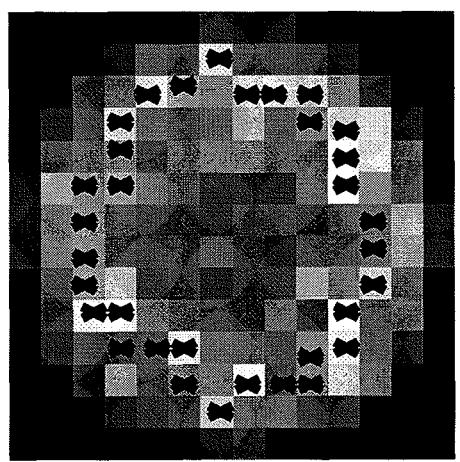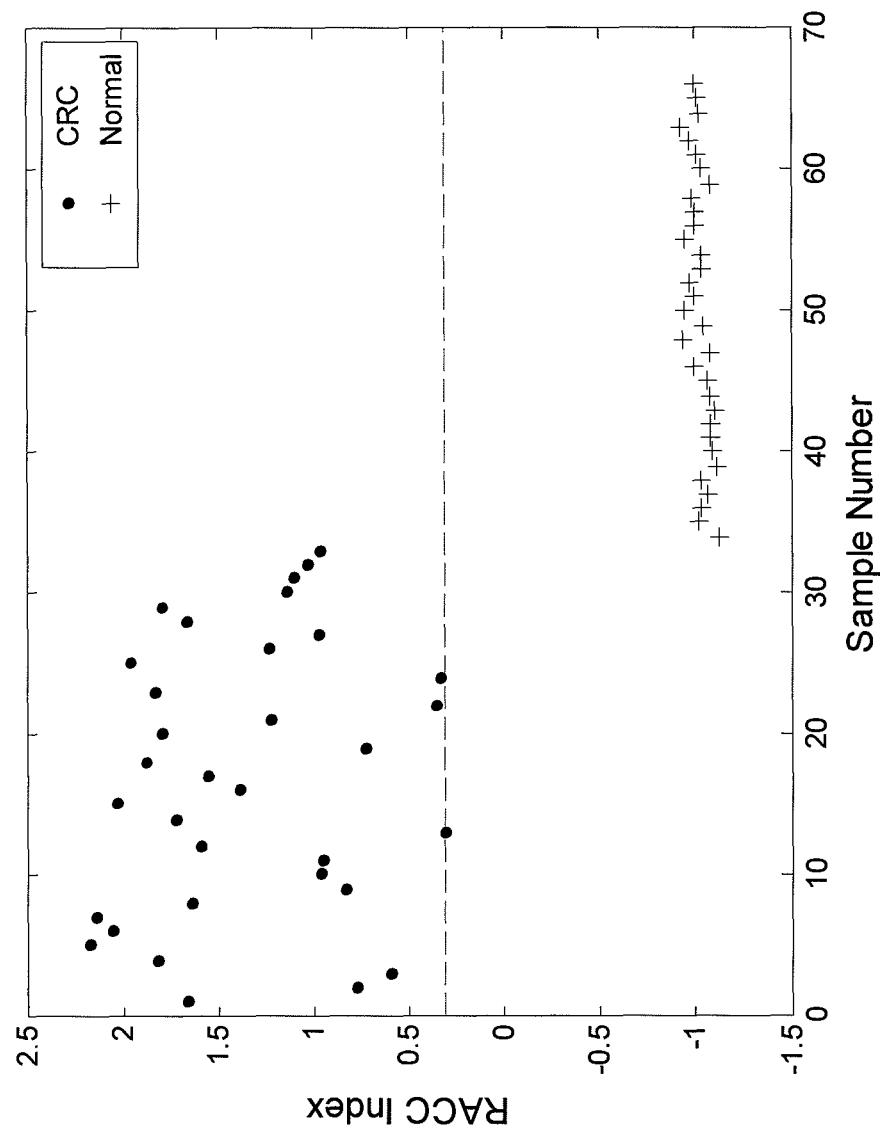
FIG. 12B

|  | Class | Mean | Std Dev | Difference Between Means | % Difference Between Means | Difference Between Std Dev | % Difference Between Std Dev |
|---|---|---|---|---|---|---|---|
| Grid Pattern | CRC | 0.9863 | 0.7286 | 1.9399 | 22% | 0.634 | -21% |
|  | Normal | -0.9536 | 0.0946 |  |  |  |  |
| Ring Pattern | CRC | 1.3393 | 0.5522 | 2.3664 |  | 0.4995 |  |
|  | Normal | -1.0271 | 0.0527 |  |  |  |  |

FIG. 12C

CRC Pt

Normal Pt

| Spectral Feature (cm⁻¹) | Assignment | α-Helix Conformation | Random Coil Conformation |
|---|---|---|---|
| 1660 | Amide I | Decreases | Increases |
| 1230-1300 | Amide III | Increase at 1263 | No change at 1263 |
| 941 | C-C Stretch of Polypeptide Backbone | Increase at 938 | No change at 938 |
| 857/827 | Tyrosine Fermi Resonance Doublet | Decrease ratio (1.1) | Increase ratio (1.2) |

FIG. 16

SYSTEM AND METHOD FOR SERUM BASED CANCER DETECTION

RELATED APPLICATIONS

This application is a U.S. national stage filing under 35 U.S.C. § 371 of International Application No. PCT/US2013/068671 filed Nov. 6, 2013 entitled "SYSTEM AND METHOD FOR SERUM BASED CANCER DETECTION," which claims priority under 35 U.S.C. 119(e) to the following provisional U.S. Patent applications: No. 61/796,268, filed on Nov. 6, 2012, entitled "System and Method for Serum Based Cancer Detection," No. 61/797,686, filed on Dec. 13, 2012, entitled "System and Method for Serum Based Cancer Detection, Staging, and Polyp Discrimination," No. 61/848,242, filed on Dec. 28, 2012, entitled "Calibration Transfer Function for Biological Materials," No. 61/765,524, filed on Feb. 15, 2013, entitled "System and Method for Determining Disease Stage Using Raman Molecular Imaging," No. 62/089,777, filed on Dec. 9, 2014, entitled "Molecular Chemical Imaging Endoscopic Imaging Systems," and No. 62/113,958, filed Feb. 9, 2015, entitled "Molecular Chemical Imaging Endoscopic Imaging Systems." All of these applications are hereby incorporated by reference in their entireties.

BACKGROUND

Cancer is significant, not only in terms of mortality and morbidity, but also in terms of the cost of treating advanced cancers and the reduced productivity and quality of life of advanced cancer patients. Despite the common conception of cancers as incurable diseases, many cancers can be alleviated, slowed, or even cured if timely medical intervention can be administered. A widely recognized need exists for tools and methods for early detection of cancer.

Cancers arise by a variety of mechanisms, not all of which are well understood. Cancers, called tumors when they arise in the form of a solid mass, characteristically exhibit decontrolled growth and/or proliferation of cells. Cancer cells often exhibit other characteristic differences relative to the cell type from which they arise, including altered expression of cell surface, secreted, nuclear, and/or cytoplasmic proteins, altered antigenicity, altered lipid envelope (i.e., cell membrane) composition, altered production of nucleic acids, altered morphology, and other differences. Typically, cancers are diagnosed either by observation of tumor formation or by observation of one or more of these characteristic differences. Because cancers arise from cells of normal tissues, cancer cells usually initially closely resemble the cells of the original normal tissue, often making detection of cancer cells difficult until the cancer has progressed to a stage at which the differences between cancer cells and the corresponding original normal cells are more pronounced. Depending on the type of cancer, the cancer can have advanced to a relatively difficult-to-treat stage before it is easily detectable.

Early definitive detection and classification of cancer is often crucial to successful treatment. Included in the diagnosis of many cancers is a determination of the type and grade of the cancer and the stage of its progression. This information can inform treatment selection, allowing use of milder treatments (i.e., having fewer undesirable side effects) for relatively early-stage, non- or slowly-spreading cancers and more aggressive treatment (i.e., having more undesirable side effects and/or a lower therapeutic index) of cancers that pose a greater risk to the patient's health.

When cancer is suspected, a physician will often have the tumor or a section of tissue having one or more abnormal characteristics removed or biopsied and sent for histopathological analyses. Typically, the time taken to prepare the specimen is on the order of one day or more. Communication of results from the pathologist to the physician and to the patient can further slow the diagnosis of the cancer and the onset of any indicated treatment. Patient anxiety can soar during the period between sample collection and diagnosis.

A recognized need exists to shorten the time required to analyze biological samples in order to determine whether or not the sample is cancerous. Furthermore, it would be beneficial to use body fluids instead of traditional tissue/cellular samples, in order to minimize patient discomfort and improve patient acceptance of testing.

Spectroscopic techniques provide information about biological molecules and therefore hold potential for providing information about the biological sample's disease state. As the biological sample's state (e.g., the sample's metabolic state) changes from a normal state to a diseased state, spectroscopic techniques may provide information to indicate the change and serve to diagnose and predict the outcome of a disease.

Various types of spectroscopy and imaging may be explored for detection of various types of diseases in particular cancers. Because Raman spectroscopy is based on irradiation of a sample and detection of scattered radiation, it can be employed non-invasively and non-destructively, such that it is suitable for analysis of biological samples. Thus, little or no sample preparation is required. In addition, water exhibits very little Raman scattering, and Raman spectroscopy techniques can be readily performed in aqueous environments.

Raman spectroscopy provides information about the vibrational state of molecules. Many molecules have atomic bonds capable of existing in a number of vibrational states. Such molecules are able to scatter incident radiation that matches a transition between two of its allowed vibrational states and to subsequently emit the radiation. Most often, scattered radiation is re-radiated at the same wavelength, a process designated Rayleigh or elastic scattering. In some instances, the re-radiated radiation can contain slightly more or slightly less energy than the incident radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in wavelength can be more easily distinguished from the Rayleigh scattered light.

The Raman spectrum of a material can reveal the molecular composition of the material, including the specific functional groups present in organic and inorganic molecules. Raman spectroscopy is useful for detection of biological materials because most, if not all, of these agents exhibit characteristic "fingerprint" Raman spectra, subject to various selection rules, by which the agent can be identified. Raman peak position, peak width, peak shape, and adherence to selection rules can be used to determine molecular identity and to determine conformational information (e.g., crystalline phase, degree of order, protein secondary structure) for condensed phase materials.

In the past several years, a number of key technologies have been introduced into wide use that have enabled scientists to largely overcome the problems inherent to Raman spectroscopy. These technologies include high efficiency solid-state lasers, efficient laser rejection filters, and silicon (Si) charge coupled device (CCD) detectors. In general, the sample size determines the choice of image gathering optic. For example, a microscope is typically employed for the analysis of submicron to millimeter spatial dimension samples. For larger objects, in the range of millimeter to meter dimensions, macro lens optics are appropriate. For samples located within relatively inaccessible environments, flexible fiberscope or rigid borescopes can be employed. For very large scale objects, such as planetary objects, telescopes are appropriate image gathering optics.

For detection of images formed by the various optical systems, two-dimensional, imaging focal plane array (FPA) detectors are typically employed. The choice of FPA detector is governed by the spectroscopic technique employed to characterize the sample of interest. For example, Si CCD detectors or complementary metal-oxide-semiconductor (CMOS) detectors are typically employed with visible (VIS) wavelength fluorescence and Raman spectroscopic imaging systems, while indium gallium arsenide (InGaAs) FPA detectors are typically employed with near-infrared (NIR) spectroscopic imaging systems.

In order to detect Raman scattered light and to accurately determine the Raman shift of that light, the sample should be irradiated with substantially monochromatic light, such as light having a bandwidth not greater than about 1.3 nanometers (nm), and preferably not greater than 1.0, 0.50, or 0.25 nm. Suitable sources include various lasers and polychromatic light source-monochromator combinations. It is recognized that the bandwidth of the irradiating light, the resolution of the wavelength resolving element(s), and the spectral range of the detector determine how well a spectral feature can be observed, detected, or distinguished from other spectral features. The combined properties of these elements (i.e., the light source, the filter, grating, or other mechanism used to distinguish Raman scattered light by wavelength) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light) can limit the ability to resolve, detect, or distinguish spectral features. The skilled artisan understands that and how the separation and shape of Raman scattering signals can determine the acceptable limits of spectral resolution for the system for any of the Raman spectral features described herein.

Spectroscopic imaging combines digital imaging and molecular spectroscopy techniques, which can include Raman scattering, fluorescence, photoluminescence, ultraviolet (UV), VIS and infrared (IR) absorption spectroscopies. When applied to the chemical analysis of materials, spectroscopic imaging is commonly referred to as chemical imaging. Instruments for performing spectroscopic (i.e. chemical) imaging typically comprise an illumination source, image gathering optics, focal plane array imaging detectors and imaging spectrometers.

For example, Raman chemical imaging (RCI) is a reagentless tissue imaging approach based on the scattering of laser light from tissue samples. The approach yields an image of a sample wherein pixels of the image is the Raman spectrum of the sample at the corresponding location. The Raman spectrum carries information about the local chemical environment of the sample at each location. RCI has a spatial resolving power of approximately 250 nm and can potentially provide qualitative and quantitative image information based on molecular composition, conformation and morphology.

Spectroscopic imaging of a sample can be implemented by one of several methods. First, a point-source illumination can be provided on the sample to measure the spectra at each point of the illuminated area. Line scanning may also be used where data is generated by illuminating a sample with a laser line. Spectra may also be collected over the entire area encompassing the sample simultaneously using an electronically tunable optical imaging filter such as an acousto-optic tunable filter (AOTF), a multi-conjugate tunable filter (MCF), or a liquid crystal tunable filter (LCTF). In an MCF, the organic material in such optical filters is actively aligned by applied voltages to produce the desired bandpass and transmission function. The spectra obtained for each pixel of such an image thereby forms a complex data set referred to as a hyperspectral image, which contains the intensity values at numerous wavelengths or the wavelength dependence of each pixel element in this image. The method selected to generate spectroscopic data may depend on a variety of factors including the nature of the sample being analyzed, time required for analysis, and cost.

The ability to determine a disease state is critical to clinical diagnosis and cancer detection. Such testing often requires obtaining the spectrum of a sample at different wavelengths. Conventional spectroscopic devices operate over a limited range of wavelengths due to the operation ranges of the detectors, tunable filters, or other system components possible. This enables analysis in the UV, VIS, IR, NIR, short wave infrared (SWIR) mid-infrared (MIR), and long wave infrared (LWIR) wavelengths and to some overlapping ranges. These correspond to wavelengths of about 180-380 nm (UV), about 380-700 nm (VIS), about 700-2500 nm (NIR), about 850-1700 nm (SWIR) and about 2500-5000 nm (MIR), and about 5000-25000 nm (LWIR). Additional techniques include attenuated total reflectance (ATR) and fluorescence.

The most effective cure for cancer is early, pre-symptomatic detection. Once the presence of cancer is obvious, such as malignant and growing tumors combined with metastasis to other organs, the survival rate is very poor, especially in the cases of colorectal cancer (CRC). Early detection of colorectal cancer, the third most common cancer in the developed world, can result in a five plus year survival rate of 95%. However, late stage detection is reported to have disconcerting survival rates of only 5% combined with end of life medical costs skyrocketing up to hundreds of thousands of dollars. To date, early stage tumor markers have not been well receive by clinicians and insurers because of their poor reliability and inconsistent relevance to specific cancerous conditions. A need exists for an accurate and reliable system and method of detecting CRC, including early stage detection. Such a solution may hold potential for detecting CRC in patients earlier than using traditional methods, monitor recurrence of CRC, and therefore allow a patient to seek treatment earlier, increasing survival rates.

SUMMARY

The present disclosure provides for a system and method for analyzing serum samples using spatially resolved Raman spectroscopy and/or Raman chemical imaging and supervised multivariate statistical analysis (i.e. chemometric) techniques to diagnose CRC and its precancerous lesions. In addition to detecting cancer, the system and method of the present disclosure may also hold potential for determining a cancer grade of a sample and to distinguish cancer from normal samples and/or the presence of polyps. Changes in the concentration or conformation of molecules in a sample may change as cancer progresses. These changes may be detected using the system and method disclosed herein and by analyzing changes in spectral bands between these stages. The disclosure provides for various embodiments comprising the use of spectroscopic, imaging, and sensor fusion techniques.

The system and method disclosed herein provide for the use of multipoint Raman spectroscopy and/or imaging in conjunction with a fiber array spectral translator (FAST) device. The use of FAST enables full spectral acquisition for hundreds to thousands of spatially resolved spectra in a single image frame. Use of a FAST device overcomes the limitations of the prior art by dramatically increasing data acquisition rates compared to point scanning or current tunable filter based technologies. Software, hardware, and/or a combination of software and hardware may be used to extract the spatial/spectral information to reconstruct data. Furthermore, FAST is a rugged technology that operates over an extensive spectral range from UV to IR. Therefore, the system and method of the present disclosure hold potential for providing a simple, low-cost, reagentless in vitro diagnostic test performed which may be performed on biological samples, such as dried blood serum samples. The analysis of dried blood serum samples also provides an advantage over other techniques for detecting CRC in that it is minimally invasive to a patient.

A system is provided for analyzing biological samples. The system may comprise an illumination source configured to illuminate at least one location of the biological sample and generate at least one plurality of interacted photons. The interacted photons may be directed to a spectrometer using at least one mirror. At least one detector may be configured to detect the interacted photons and generate at least one Raman data set representative of the biological sample. At least one processor may be configured to analyze the Raman data set and associate the biological sample with at least one disease state.

A method is provided that comprises illuminating at least one location of a biological sample to generate at least one plurality of interacted photons. The interacted photons may be collected and detected to generate at least one Raman data set representative of the biological sample. The Raman data set may be analyzed to associate the biological sample with at least one disease state.

The present disclosure also provides for a non-transitory storage medium containing machine readable program code, which, when executed by a processor, causes the processor to perform the following: illuminate at least one location of a biological sample to generate at least one plurality of interacted photons, collect the plurality of interacted photons, detect the plurality of interacted photos and generate at least one Raman data set representative of the biological sample, and analyze the Raman data set to associate the biological sample with at least one disease state.

BRIEF DESCRIPTION OF THE DRAWINGS

The accompanying drawings, which are included to provide further understanding of the disclosure and are incorporated in and constitute a part of this specification illustrate embodiments of the disclosure, and together with the description, serve to explain the principles of the disclosure.

In the drawings:

FIG. 7A is illustrative of a low throughput sampling configuration of one embodiment of the present disclosure.

FIG. 7B is illustrative of a high throughput sampling configuration of one embodiment of the present disclosure.

FIG. 12A is illustrative of the detection capabilities of the present disclosure to differentiate between CRC and normal samples using RCI data in a grid pattern sampling configuration.

FIG. 12B is illustrative of the detection capabilities of the present disclosure to differentiate between CRC and normal samples using RCI data in a ring pattern sampling configuration.

FIG. 12C is illustrative of statistical information relating to the sampling configurations illustrated in FIG. 12A and FIG. 12B.

FIG. 16 is illustrative of exemplary spectral features of interest relating to assessing protein conformation.

DETAILED DESCRIPTION

Reference will now be made in detail to the embodiments of the present disclosure, examples of which are illustrated in the accompanying drawings. Wherever possible, the same reference numbers will be used throughout the specification to refer to the same or like parts.

The present disclosure provides for a system and method for analyzing biological samples or components of biological samples. Examples of biological samples include, but are not limited to, a bodily fluid such as urine, saliva, sputum, feces, blood, serum, plasma, mucus, pus, semen, fluid expressed from a wound, lavage, cerebrospinal fluid, vaginal fluid, and combinations thereof. Although this disclosure focuses on determining a disease state (detecting cancer or a normal sample) of a biological sample, the present disclosure also contemplates that the system and method disclosed herein may be used to determine other characteristics of a sample (e.g. a metabolic state, a hydration state, an inflammatory state, and combinations thereof) and precursor conditions such as the presence of polyps within its definition of disease state. Additionally, while the examples provided herein relate to the detection of CRC, the present disclosure is not limited to CRC and the system and method may be used to detect a wide variety of cancers. In addition to detecting whether or not a sample comprises cancer, the system and method may also be applied to determine a cancer grade (or disease grade).

Figure 1:
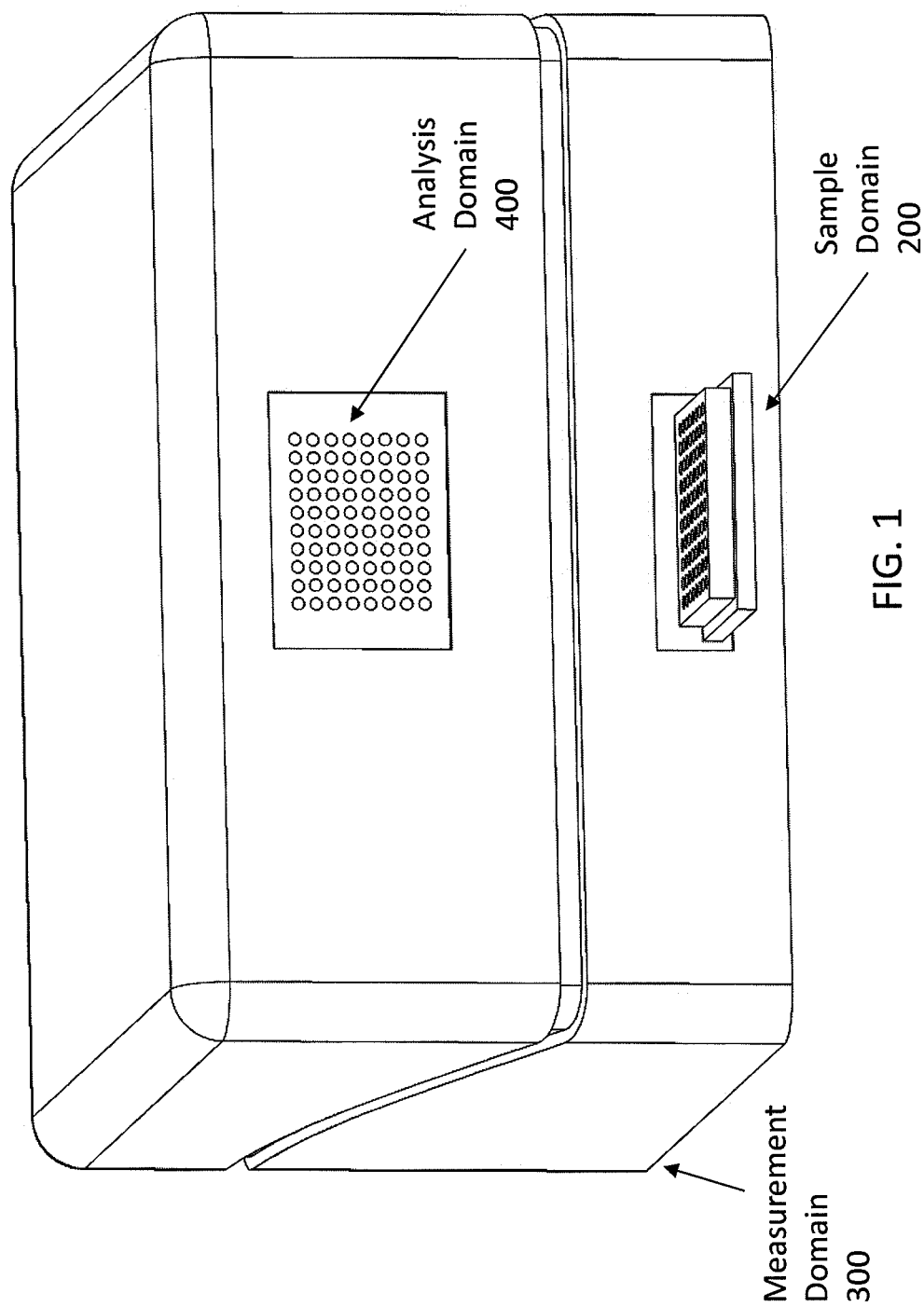
FIG. 1 is illustrative of an exemplary housing configuration of a system of the present disclosure.

The present disclosure provides for a system, further illustrated by FIGS. 1-4 for analyzing biological samples to determine a disease state. An exemplary housing of a system 100 is illustrated in FIG. 1. As can be seen in FIG. 1, the system 100 may comprise a sample domain 200 for placing a sample under analysis, a measurement domain 300, for generating at least one Raman data set representative of the sample placed in the sample domain 200, and an analysis domain 400 for analyzing the data generated by the measurement domain 300.

Figure 2:
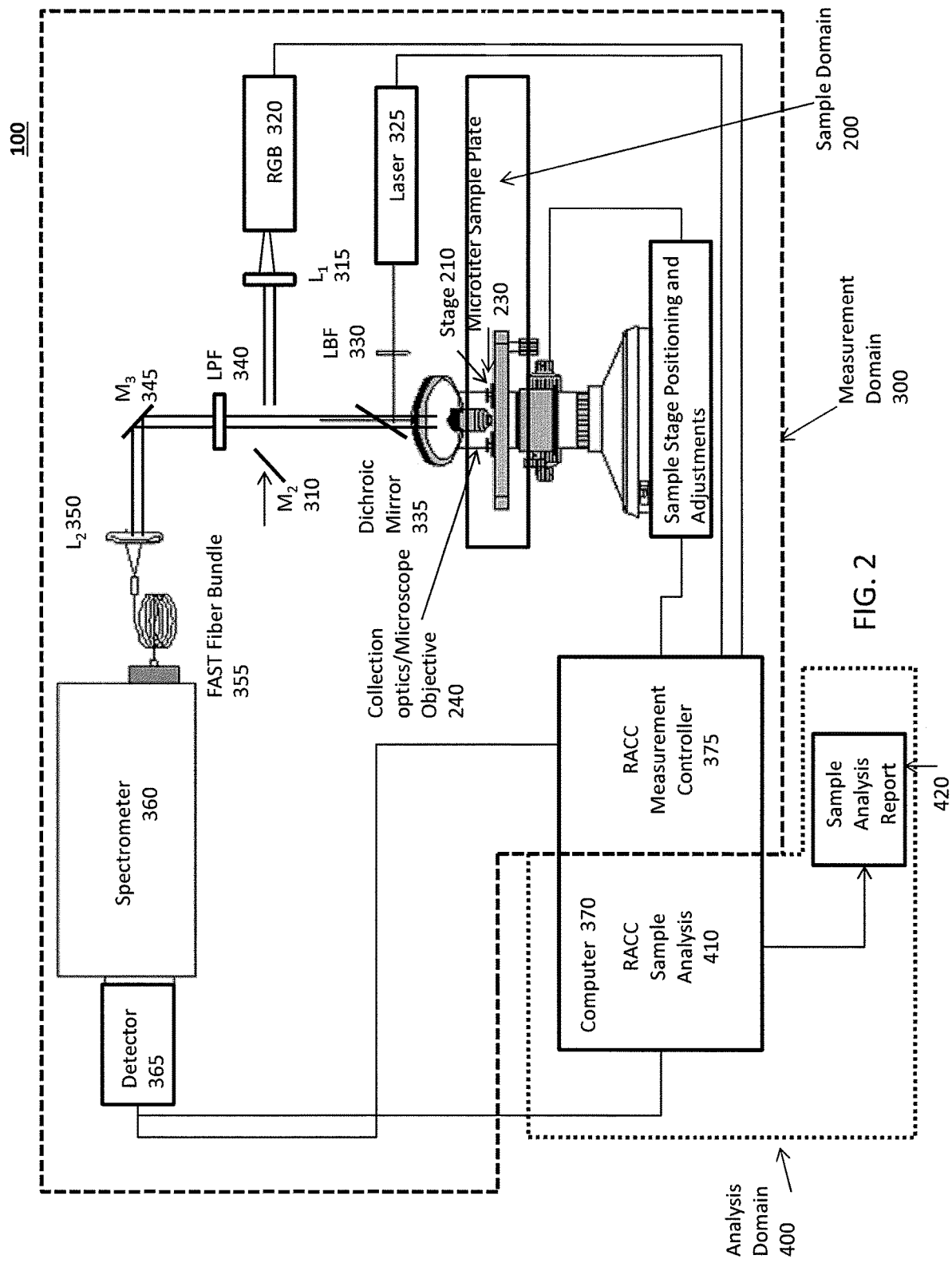
FIG. 2 is illustrative of a system of the present disclosure.

FIG. 2 is a more detailed representation of a system 100 of the present disclosure. As illustrated in FIG. 2, the sample domain 200 may further comprise a stage 210 for placing a sample. This stage 210 may be moved to analyze the various samples under analysis. In one embodiment, the sample may be affixed to a slide or placed in a well plate, such as a microtiter sample plate 230. The sample may be placed under collection optics such as a microscope objective 240 for analysis.

The measurement domain 300 may comprise an RGB camera 320 configured to generate an RGB image representative of the sample. At least one mirror 310 may be configured to direct photons from the sample through at least one lens 315 to the RGB camera 320. The RGB image generated may be used to help align the sample for analysis and/or be used to find morphological features or areas of interest in the sample. The RGB image may also be correlated with a Raman data set generated by the measurement domain 300.

Still referring to FIG. 2, the measurement domain 200 may further comprise at least one laser illumination source 325 configured to emit illuminating photons that may be passed through a laser bandpass filter (LBF) 330 to filter out wavelengths of light that are not of interest and allow one or more wavelengths of light of interest to pass through. These filtered illuminating photons may be directed to the sample by at least one mechanism 335 such as a dichroic mirror or a dichroic beamsplitter.

The illuminating photons may illuminate the sample and generate at least one plurality of interacted photons. In one embodiment, these interacted photons may comprise at least one of: photons scattered by the sample, photons absorbed by the sample, photons reflected by the sample, photons emitted by the sample, and combinations thereof.

Figure 3A:
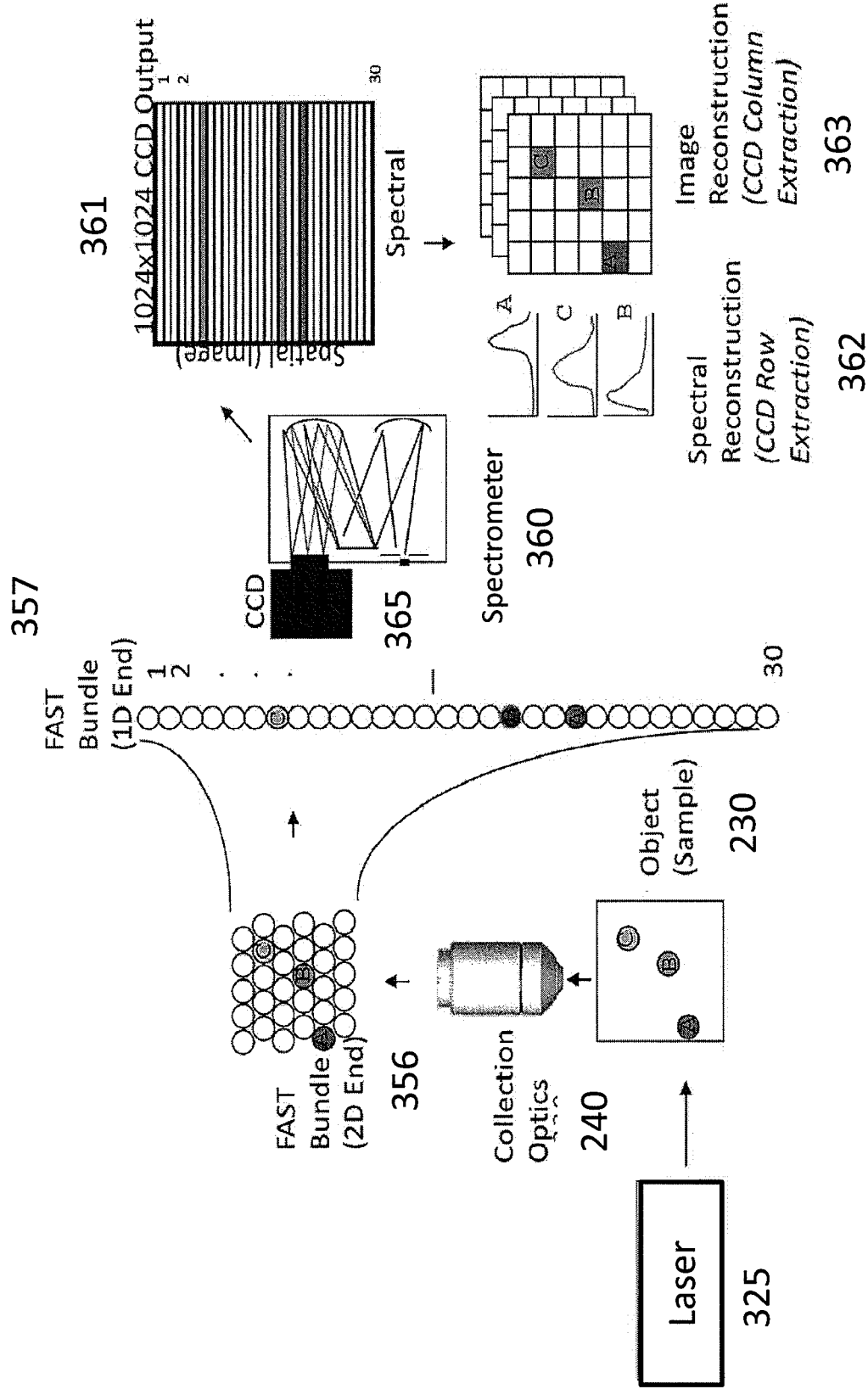
FIG. 3A is illustrative of a fiber array spectral translator (FAST) device of the present disclosure.

The plurality of interacted photons may be passed through a long pass filter (LPF) 340 to filter out photons having short wavelengths and directed by at least one mirror 345 through a lens 350 to a two-dimensional end of a FAST device 355. A FAST device 355 is illustrated in more detail in FIG. 3A. In FIG. 3A, the FAST device 355 comprises a two-dimensional end 356 and a one-dimensional end 357. In one embodiment, the two-dimensional end 356 may have an ordering such as serpentine ordering. The two-dimensional end 356 of the FAST device 355 may comprise a two-dimensional array of optical fibers drawn into a one-dimensional fiber stack 357. In one embodiment, the two-dimensional end 365 may be non-linear (which can be in any non-linear configuration, e.g., circular, square, rectangular, etc.) and the one-dimensional linear end 357 may be linear.

Interacted photons may be focused onto the input (two-dimensional end 365) of a FAST device, which may consist of up to thousands of individual fibers, each fiber collecting the light scattered (or absorbed, reflected, and/or emitted) by a specific corresponding location in the excited area of a biological sample.

The one-dimensional fiber stack 357 (output end) may be orientated at the entrance slit of a spectrometer 360, illustrated in both FIG. 2 and FIG. 3A. The spectrometer 360 can function to separate the plurality of photons into a plurality of wavelengths and provide a separate dispersive spectrum from each fiber. Multiple Raman spectra and therefore multiple interrogations of the sample area can be obtained in a single measurement cycle, in essentially the same time as in conventional Raman sensors.

Referring to FIG. 2, the photons may be detected at a detector 365 to generate a Raman data set representative of a biological sample. In one embodiment, a processor (and/or software) 370 may be used to extract spectral/spatial information that is embedded in a single frame generated by a detector 365.

Referring to FIG. 3A, 361 is representative of an exemplary detector 365 output, 362 is representative of an exemplary spectral reconstruction, and 363 is representative of an exemplary image reconstruction.

In one embodiment, an area of interest can be optically matched by the FAST device to an area of a laser spot to maximize the collection Raman efficiency. In one embodiment, the present disclosure contemplates a configuration in which only the laser beam is moved for scanning within a field of view (FOV). The present disclosure also contemplates a preferred embodiment, wherein the sample is moved and the laser beam is stationary.

It is possible to optically match the "scanning" FOV with the Raman collection FOV. The FOV is imaged onto a rectangular FAST device so that each FAST fiber is collecting light from one region of the FOV. The area per fiber which yields the maximum spatial resolution is easily calculated by dividing the area of the entire FOV by the number of fibers. Raman scattering is only generated when the laser excites a sample, so Raman spectra will only be obtained at those fibers whose collection area is being scanned by the laser beam. Scanning only the laser beam is a rapid process that may utilize off the shelf galvonmeter-driven mirror systems.

The construction of the FAST device 355 requires knowledge of the position of each fiber at both the two-dimensional end 356 and the distal end, one-dimensional end 357 of the array. Each fiber collects light from a fixed position in the two-dimensional array (imaging end) and transmits this light onto a fixed position on the detector 365 (through that fiber's distal end 357).

Each fiber may span more than one detector row, allowing higher resolution than one pixel per fiber in the reconstructed image. In fact, this super-resolution, combined with interpolation between fiber pixels (i.e., pixels in the detector associated with the respective fiber), achieves much higher spatial resolution than is otherwise possible. Thus, spatial calibration may involve not only the knowledge of fiber geometry (i.e., fiber correspondence) at the imaging end and the distal end, but also the knowledge of which detector rows are associated with a given fiber.

One of the fundamental advantages of using a FAST device, over other spectroscopic methods, is speed of analysis. FAST technology can acquire a few to thousands of full spectral range, spatially resolved spectra simultaneously. A complete spectroscopic imaging data set can be acquired in the amount of time it takes to generate a single spectrum from a given material, especially for samples that are susceptible to laser induced photodamage. FAST devices can also be implemented with multiple detectors and color-coded FAST spectroscopic images can be superimposed on other high-spatial resolution gray-scale images to provide significant insight into the morphology and chemistry of the sample.

Utilizing a FAST device is one way of configuring a system 100 for what may be referred to as "multipoint" analysis. To perform multipoint analysis, the biological sample and field to be evaluated is illuminated in whole or in part, depending on the nature of the biological sample and the type of multipoint sampling desired. A field of illumination can be divided into multiple adjacent, non-adjacent, or overlapping points, and spectra can be generated at each of the points. In one embodiment, these spectra may be averaged. In another embodiment, an illumination spot size can be increased sufficiently to spatially sample/average over a large area of the sample. This may also include transect sampling.

By way of example, the entire sample can be illuminated and multipoint analysis performed by assessing interacted photons at selected points. Alternatively, multiple points of the sample can be illuminated, and interacted photons emanating from those points can be assessed. The points can be assessed serially (i.e., sequentially). To implement this strategy, there is an inherent trade off between acquisition time and the spatial resolution of the spectroscopic map. Each full spectrum takes a certain time to collect. The more spectra collected per unit area of a sample, the higher the apparent resolution of the spectroscopic map, but the longer the data acquisition takes. In another embodiment, interacted photons can be assessed in parallel (i.e., simultaneously) for all selected points in an image field. This parallel processing of all points is designated chemical imaging, and can require significant data acquisition time, computing time and capacity when very large numbers of spatial points and spectral channels are selected, but require less data acquisition time, computing time and capacity when relatively small number of spectral channels are assessed.

Figure 3B:
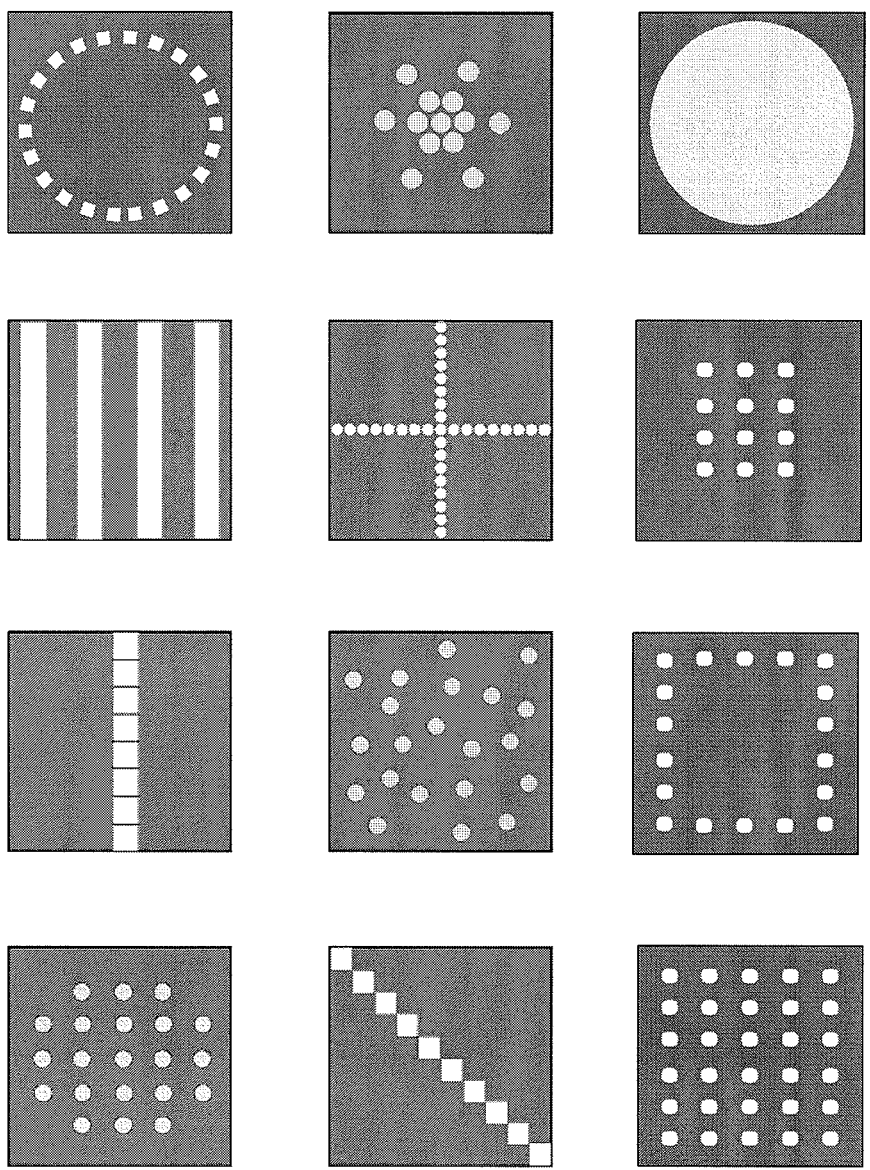
FIG. 3B is illustrative of exemplary sampling configurations of various embodiments of the present disclosure.

The present disclosure provides for assessing interacted photons at multiple points in a FOV (e.g., the field of magnification for a microscope) that together represent only a portion of the area of the FOV (multipoint). It has been discovered that sampling the FOV at points representing a minority of the total area of the field (e.g., at two, three, four, six, ten, fifty, one hundred, or more) points representing, in sum, 25%, 5%, 1%, or less of the field). The points can be single pixels of an image of the FOV or areas of the field represented in an image by multiple adjacent or grouped pixels. The shape of areas or pixels assessed as individual points is not critical. For example, circular, annular, square, or rectangular areas or pixels can be assessed as individual points. Lines of pixels may also be assessed in a line scanning configuration. FIG. 3B is illustrative of exemplary sampling configurations of the various embodiments of the present disclosure.

The area corresponding to each point of a multipoint analysis can be selected or generated in a variety of known ways. In one embodiment, structured illumination may be used. By way of example, a confocal mask or diffracting optical element placed in the illumination or collection optical path can limit illumination or collection to certain portions of the sample having a defined geometric relationship.

Spectroscopic analysis of multiple points in a FOV (multipoint analysis) allows high quality spectral sensing and analysis without the need to perform spectral imaging at every picture element (pixel) of an image. Optical imaging (e.g. RGB imaging) can be performed on the sample (e.g., simultaneously or separately) and the optical image can be combined with selected spectral information to define and locate regions of interest. Rapidly obtaining spectra from sufficient different locations of this region of interest at one time allows highly efficient and accurate spectral analysis and the identification of components in samples. Furthermore, identification of a region of interest in a sample or in a FOV can be used as a signal that more detailed Raman scattering (or other) analysis of that portion of the sample or FOV should be performed.

The high numbers of optical fibers required for FAST spectroscopic and/or imaging applications place extraordinary demands on the imaging spectrograph which the multipoint method addresses. Instead of having millions of pixels, multipoint analysis can utilize larger diameter fibers in bundles containing two to thousands of fibers. In the multipoint method of spectral sensing and analysis, complete spectral imaging (which would require at least thousands of adjacent pixels to create a physical image) is not required. Instead, spectral sensing performed at two to thousands of points simultaneously can rapidly (on the order of seconds) provide high quality spatially resolved spectra from a wide variety of points on the sample needed for analysis and identification. Thus, even if the precise geometric arrangement of the points analyzed in the FOV is not known, the points nonetheless have a defined geometrical arrangement which can span a sample or a FOV. The analyzed points may be informative regarding the disease state of a biological sample.

Referring again to FIG. 2, photons may be delivered to a spectrometer 360 wherein the spectrometer is configured to filter the interacted photons into a plurality of wavelengths. A detector 365 may be configured to generate at least one Raman data set representative of the sample. In one embodiment, the Raman data set may comprise at least one of: at least one Raman spectrum and at least one Raman chemical image. In one embodiment, the detector 365 may further comprise at least one of: a CCD detector, an intensified charge coupled device (ICCD) detector, an InGaAs detector, an indium antimonide (InSb) detector, and a mercury cadmium telluride (MCT) detector.

The system 100 may further comprise at least one processor 370. The processor 370 may function to carry out various functions in both the measurement domain 300 and the analysis domain 400. In the measurement domain 300, the processor 370 may comprise a measurement controller 375 that may comprise software to control various features of the system 100 such as data acquisition and calibration of the system 100.

The system 100 may also comprise an analysis domain 400, configured to analyze the data generated by the measurement domain 300. The processor 370 may function in the analysis domain 400 to analyze the Raman data set. An analysis report 420 may be generated based on this analysis. This analysis report 420 may comprise a determination of disease state of a biological sample under analysis.

In one embodiment, the system 100 may further comprise at least one reference database comprising at least one reference data set, wherein each reference data set is associated with a known disease state. This reference data may be stored in the processor 370 and accessed to analyze the Raman data set generated from the biological sample.

Figure 4:
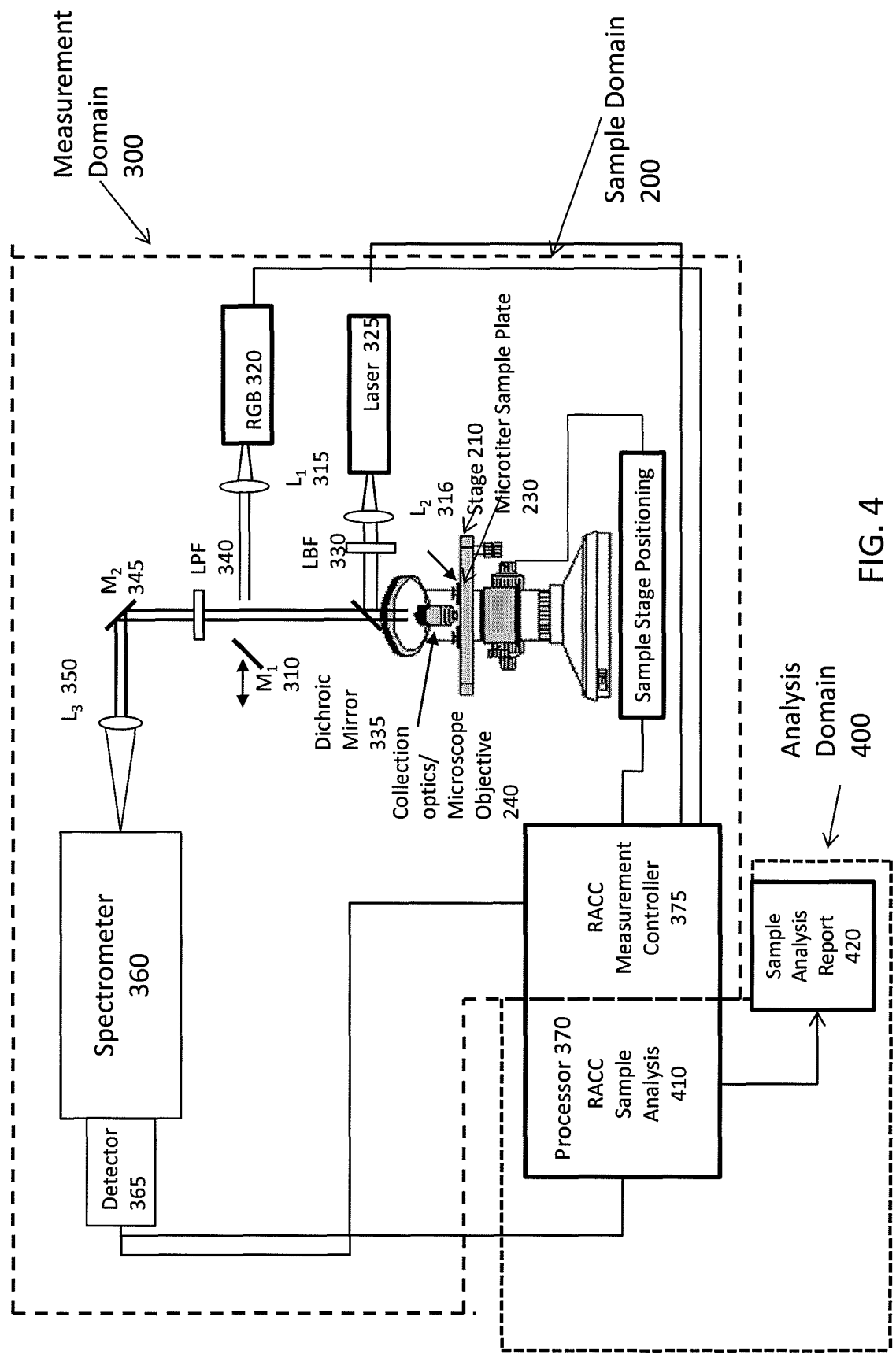
FIG. 4 is illustrative of a system of the present disclosure.

FIG. 4 is provided to illustrate another embodiment of a system 100 of the present disclosure. In the embodiment of FIG. 4, the system 100 does not comprise a FAST device 355, but rather operates using a line scanning configuration. Here, interacted photons are directed directly to a spectrometer 360. Other aspects of the system 100 may be the same as those in the embodiment of FIG. 2.

The present disclosure also provides for a method for analyzing biological samples to determine a disease state. In one embodiment, the biological sample may comprise at least one tissue. The present disclosure contemplates that this tissue may comprise a body fluid, such as blood, or a component of a tissue such as serum or plasma. When analyzing a tissue component, a method of the present disclosure may comprise processing a biological sample prior to analysis to remove any cellular or other debris from the sample. Analysis of body fluids holds potential for providing a less invasive mechanism of detecting disease than traditional biopsy methods.

Figure 5A:
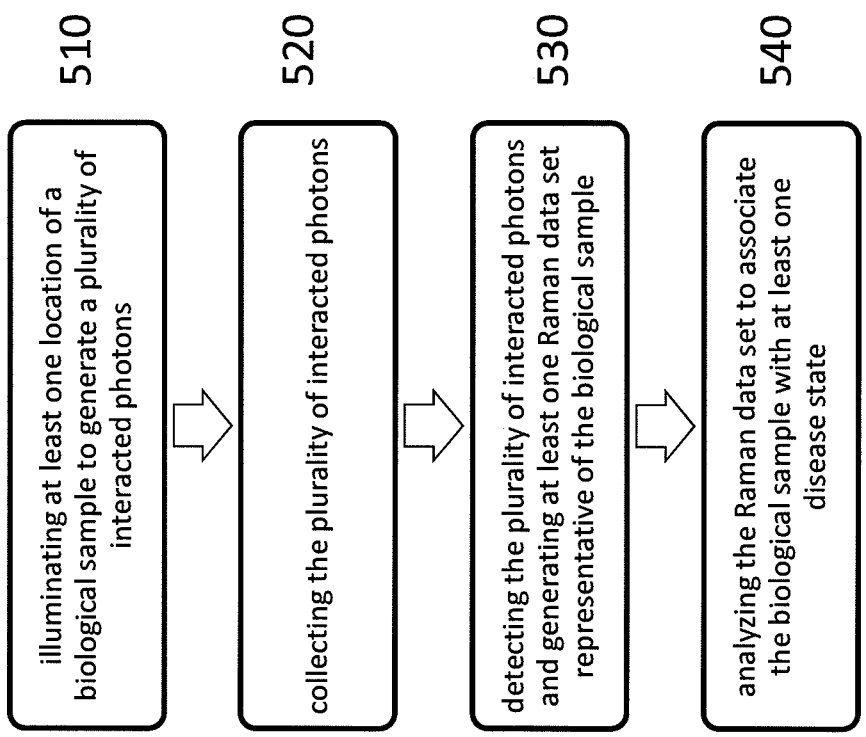
FIG. 5A is illustrative of a method of the present disclosure.

One embodiment of a method of the present disclosure is illustrated in FIG. 5. In such an embodiment, the method 500 may comprise illuminating at least one location of a biological sample to generate at least one plurality of interacted photons in step 510. These interacted photons may comprise at least one of: photons scattered by the biological sample, photons absorbed by the biological sample, photons reflected by the biological sample, and photons emitted by the biological sample.

In step 520, the plurality of interacted photons may be collected. In one embodiment, the plurality of interacted photons may be passed through a FAST device to a spectrometer. In another embodiment, wherein a line scanning approach is used, the plurality of interacted photons may be passed directly to a spectrometer without the use of a FAST device. In either embodiment, the spectrometer may be configured to separate the plurality of interacted photons into a plurality of wavelengths.

In step 530 the plurality of interacted photons may be detected to generate at least one Raman data set representative of the biological sample. The present disclosure contemplates this Raman data set may comprise at least one of: at least one Raman spectrum and at least one Raman chemical image. In step 540, the Raman data set may be analyzed to associate the biological sample with at least one disease state. In one embodiment, the disease state may comprise at least one of: cancer, normal, and the presence of polyp. Where the disease state comprises cancer, analyzing the biological sample may further comprise determining at least once cancer grade. Where the disease state comprises normal, the method may further comprise determining at least one non-cancerous condition associated with the biological sample. In one embodiment, the present disclosure contemplates generating multiple data sets for each patient over time. In such an embodiment, the system and method disclosed herein may be utilized to analyze biological samples for not only screening patients for cancer but also to monitor patients for recurrence, disease progression, or remission.

The present disclosure contemplates the determination of a disease state may be achieved by assessing one more component of a biological sample. Examples of components that may be measured include, but are not limited to: a chemical agent, a biological toxin, a microorganism, a bacterium, a protozoan, a virus, a protein, a flavonoid, a keratinoid, a metabolite, an enzyme, an electrolyte, a nucleic acid, and combinations thereof. The conformation of proteins in a biological sample (ordered or disordered) may also be analyzed.

Examples of metabolites that may be measured include, but are not limited to: those associated with the TCA cycle (succinate, isocitrate, citrate), tryptophan metabolism, (5-hydrozytryptophan, 5-hydroxyindolecetate, tryptophan), gut flora metabolism (2-hydroxyhippurate, phenlylacetatem phenylacetylglutamine, p-hydroxyphenyacetate, p-cresol), and others (5-oxoproline, N-acetyl-aspatem 3-methyl-histidine, histidine, myristate, putrescine, kynurenate). Examples of nucleic acids that may be analyzed include, but are not limited to: SEPT9 methylated DNA, non-specific RNA SERS, secreted and cell surface gene. Other analytes that may be measured include but are not limited to CEA, CA-19, E-selectin, nucleosomes, and combinations thereof. In one embodiment, the present disclosure provides for analyzing trace level analytes modulating the blood serum proteins present in the biological sample.

Figure 5B:
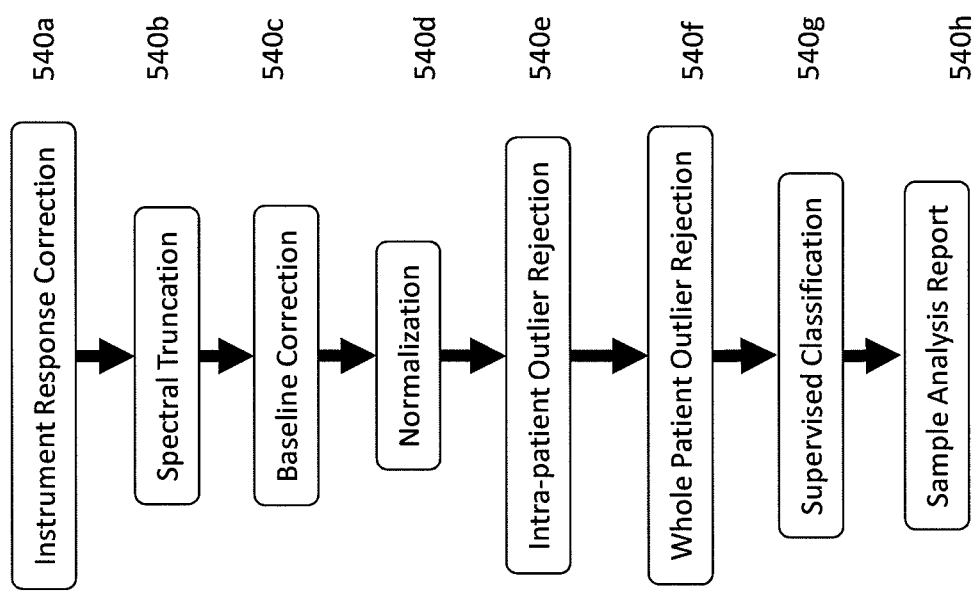
FIG. 5B is illustrative of a method of the present disclosure.

In one embodiment, analyzing the biological sample 540 may further comprise the steps represented in FIG. 5B. In such an embodiment, analyzing 540 may comprise applying an instrument response correction in step 540a. In one embodiment, an instrument response correction may further comprise at least one calibration transfer function to align misaligned spectra.

A calibration transfer function may comprise generating two or more spectral data sets representative of at least one biological sample. Reference points on the spectra may be selected where the points are common to both sets of spectra to determine a calibration transfer. As disclosed herein, a nonlinear spectral shift may exist between different data populations due to instrument and/or sample differences. In one embodiment, four spectral peaks corresponding to 1002 $cm^{-1}$, 1035 $cm^{-1}$, 1450 $cm^{-1}$, and 1672 $cm^{-1}$ may be selected. However, the present disclosure is not limited to these wavelengths and others may be applied. A piecewise linear correction is then applied to the data using these known peaks as reference points to shift and stretch the spectra. In one embodiment, the spectra may then be combined into a single data set for analysis.

Instrument factors cause interference to low-intensity spectra. Removal of these factors may reveal subtle Raman signals. These factors may be removed by comparing the collected and empirical spectra of a standard reference material. Other processing steps may be applied such as cosmic correction and flatfielding. Cosmic events occur randomly and may be seen as bright pixels in an image. For example, cosmic events may be removed by using a median filter that compares nearby neighboring pixels. Flatfielding is a process that may be used to improve uniformity of signal across the illuminated FOV. This may be performed by determining the illuminating pattern over a standard uniform material and then extracting this pattern from the sample images.

Referring again to FIG. 5B, spectra may be processed, which may include spectral truncation 540b, baseline correction 540c, and vector normalization 540d, which are known in the art. Baseline correction removes variability in the data due to fluctuating baseline, which may be affected by several factors including tissue fluorescence and background interference. For example, the first two spectral data points and the last two spectral data points may be offset to the zero baseline. Normalization places spectra on the same intensity scale so that they can be directly compared. One method of normalization renders integrated area under the spectra that are equal for all data.

The analysis 540 may further comprise applying one or more steps to remove outlier data or data that is not suitable for analysis (sampling error, etc.). In step 540e, intra-patient outlier rejection may be applied to the data to remove from analysis outlier spectra from the patient data. In step 540f, whole-patient outlier rejection may be applied to remove all data associated with a patient if it is not suitable for analysis.

In step 540g, at least one algorithm may be applied to perform supervised classification of the data. This algorithm may comprise support vector machines (SVM) and/or relevance vector machines (RVM). In another embodiment, the algorithm may comprise at least one chemometric technique. Examples of chemometric techniques that may be applied include, but are not limited to: multivariate curve resolution, principle component analysis (PCA), k means clustering, band target entropy minimization (BTEM) method, adaptive subspace detector, cosine correlation analysis, Euclidian distance analysis, partial least squares regression, spectral mixture resolution, a spectral angle mapper metric, a spectral information divergence metric, a Mahalanobis distance metric, and spectral unmixing.

In one embodiment, the cheometric technique may comprise partial least squares discriminant analysis (PLSDA). A prediction from PLSDA is usually a value between zero and one, where one indicates membership within a class and zero indicates non-membership within a class.

In one embodiment, a model may be built repeatedly using a "leave one patient out" (LOPO) cross validation until all samples have been tested. To further analyze the results, ROC curves may be generated. A ROC curve is a plot of sensitivity and specificity and may be used as a test to select a threshold score that maximizes sensitivity and specificity.

Partial Least Squares (PLS) factor selection is an important step in PLSDA model building/evaluation process. The retention of too many PLS factors leads to overfitting of the class/spectra data which may include systematic noise sources. The retention of too few PLS factors leads to underfitting of the class/spectra data. A confusion matrix is typically employed as a Figure or Merit (FOM) for the optimal selection of PLS factors. A misclassification rate for the PLSDA model is evaluated as a function of PLS factors retained. The misclassification rate, although an important parameter, is not very descriptive of the final ROC curve which is the basis for model performance. This method uses an alternative FOM for the optimal selection of PLS factors based upon parameters from the ROC curve such as the Area Under the ROC (AUROC) as well as the minimum distance to an ideal sensor. This approach overcomes the limitations of the prior art because ROC curves are not currently used for selecting factors. The ROC curve is traditionally created at the end of an evaluation process to determine the performance of the model, not to select parameters for building the model.

Referring again to FIG. 5B, a sample analysis report may be generated in step 540h. This analysis report may be generated by the RACC sample analysis 410 functionality of a processor 370, while operating in an analysis domain 400. The analysis report may comprise a determination of a disease state, cancer grade, or other conclusion drawn from the analysis of the biological sample.

The analysis report generated in step 540h may also comprise a RACC index representative of the biological sample under analysis. Here, analyzing the biological sample 540 may further comprise computing a RACC index for each biological sample. This RACC index represents a score for cancer and may be generated by applying at least one algorithm. In order to predict the class membership of a sample (e.g. cancer or normal), a threshold needs to be determined from the training data. Any sample with a RACC index above the threshold will be classified as cancer, and any sample with a RACC index below the threshold will be classified as normal. The threshold corresponds to the optimal operating point on the ROC curve that is generated by processing the training data. It is selected such that the performance of the classifier is as close to an ideal sensor as possible. An ideal sensor has a sensitivity of 100%, a specificity equal to 100%, an AUROC of 1.0, and is represented by the upper left corner of the ROC plot. To select the optimal operating point, a threshold is swept across the observed RACC indices. The true positive, true negative, false positive, and false negative classifications are calculated at each threshold value to yield the sensitivity and specificity results. The optimal operating point is the point on the ROC curve that is the minimum distance from the ideal sensor. The threshold that corresponds to this sensitivity and specificity is selected as the threshold for the model. Alternatively, the threshold can be calculated by using a cluster method, such as Otsu's method. A histogram may be calculated using the RACC indices from the training data, and Otsu's method splits the histogram into two parts or classes.

In one embodiment, the method 500 may further comprise generating at least one additional spectroscopic and/or imaging data set representative of the sample using a modality other than Raman. For example, the method 500 may further comprise generating at least one RGB image representative of the biological sample. This RGB image may be used to assess locations and/or features of interest within the sample. The RGB image may also be correlated with a Raman data set.

In addition to augmenting Raman data sets with RGB images, the present disclosure also contemplates that the method 500 may further comprise applying data fusion. In such an embodiment, other spectroscopic and/or imaging techniques may be combined with Raman data to augment the data and analyze biological samples to determine a disease state.

For example, one option for implementing data fusion is to use both Raman and fluorescence modalities and fuse the scores from each sensor using a method such as Image Weighted Bayesian Fusion (IWBF). In one embodiment, Monte Carlo methods may be used to find a set of weights which minimized the number of false positive pixels in the fused detection image when the detection threshold was set to find all the true positive pixels. The terms can also be combined using other methods such as linear regression, neural networks, fuzzy logic, etc.

Fusion often provides better discrimination performance and allows for improvements on the score distribution. Fusion can create distributions with a smaller range and variance than results from individual sensors. This can be beneficial because the threshold that is selected to discriminate the two classes relies heavily on the distribution of scores within a class. The tighter the distribution of scores is within a class and the larger difference between the classes, the better the performance of the model will be.

In embodiments utilizing sensor fusion, the system embodiments illustrated in FIGS. 2 and 4 may be altered to provide for additional components to enable generation of data using different spectroscopic and/or imaging modalities. For example, in an embodiment where fluorescence data is fused to Raman data, additional components may comprise a fluorescence light source and one or more dichroic mirrors and/or beamsplitters to direct illuminating photons to a biological sample and to direct interacted photons to the appropriate detectors. In one embodiment, a Rayleigh rejection filter may be used to filter interacted photons before being directed to a FAST device and/or to a spectrometer. The present disclosure also contemplates that other filters may be used.

Figure 6A:
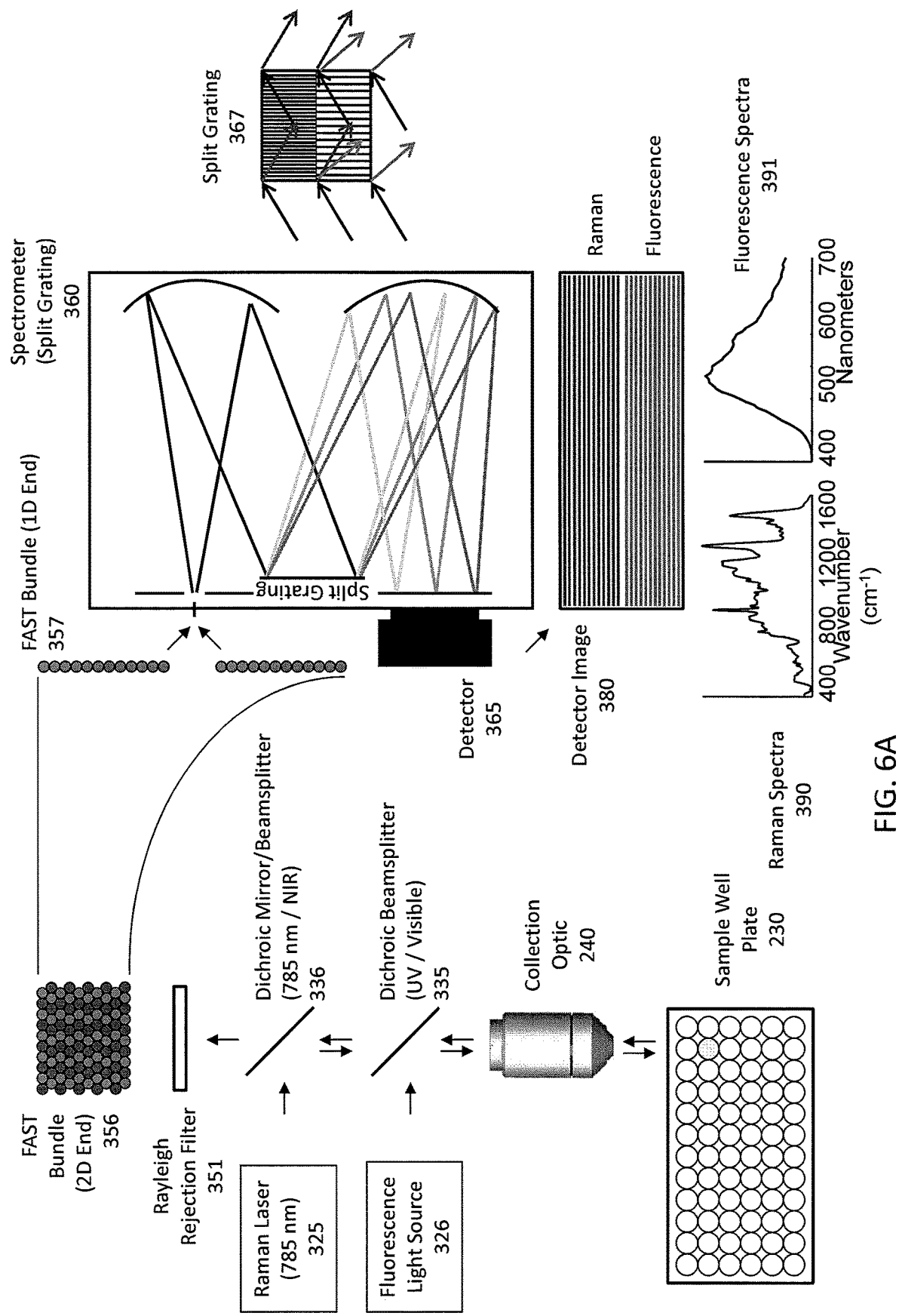
FIG. 6A is illustrative of one embodiment of a system of the present disclosure utilizing data fusion from multiple spectroscopic modalities.
Figure 6B:
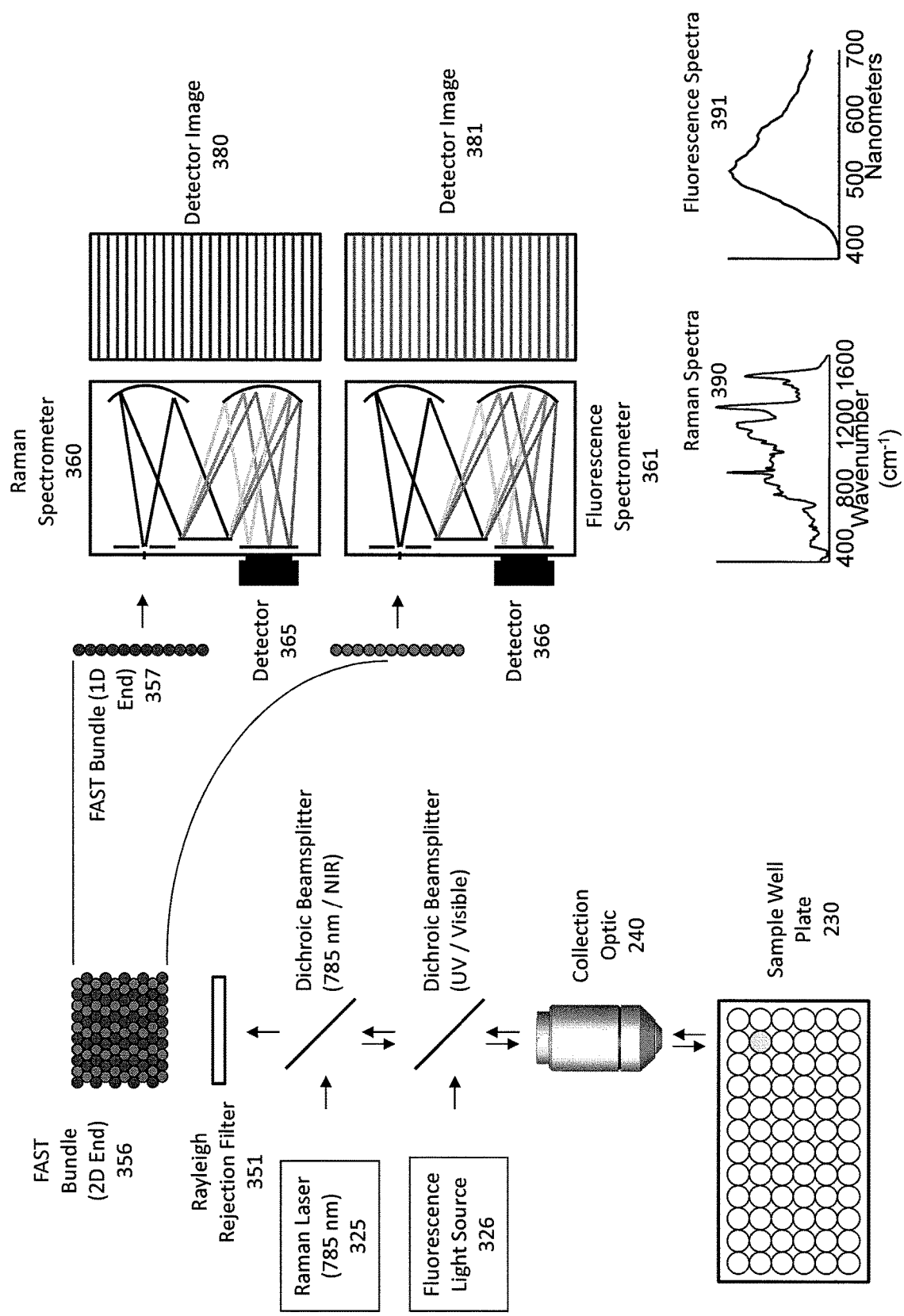
FIG. 6B is illustrative of one embodiment of a system of the present disclosure utilizing data fusion from multiple spectroscopic modalities.

FIGS. 6A and 6B are provided to further illustrate potential system configurations for data fusion. FIGS. 6A and 6B are intended to further enhance the system in FIGS. 2 and 4, and the same reference characters are used to refer to same or like parts. In FIG. 6A, one spectrometer 360 and one detector 365 may be used. Here, an additional illumination source, a fluorescence light source, 326 is provided to illuminate at least one location of a sample, for example in a well plate 230. Interacted photons generated may be passed through collection optic 240 and be directed via at least one dichroic mirror/beamsplitter 336 through a Rayleigh rejection filter 351 and to the two-dimensional end 356 of a FAST device 355. In this embodiment, the spectrometer 360 may comprise a split grating spectrometer. A split grating spectrometer 360 is illustrated in more detail by 367. The photons may be separated into a plurality of wavelengths by the spectrometer 360 and detected by a detector 365 to generate both a Raman data set and a fluorescence data set, wherein the fluorescence data set may comprise at least one of: at least one fluorescence spectrum and at least one fluorescence chemical image. An exemplary detector image is illustrated by 380 and exemplary Raman and fluorescence spectra are illustrated by 390 and 391.

Another embodiment utilizing Raman/fluorescence data fusion is illustrated in FIG. 6B. Here, two separate spectrometers, 360 and 361 are configured to receive interacted photons from the one-dimensional end 357 of a FAST device 355. Each spectrometer may filter the interacted photons into a plurality of wavelengths and two detectors, 365 and 366, may be configured to detect these photons. One detector 365 may be configured to generate a Raman data set and the other detector 366 may be configured to generate a fluorescence data set. Exemplary detector images are illustrated by 380 and 381. Exemplary Raman spectra are illustrated by 390 and exemplary fluorescence spectra are illustrated by 391.

In addition to the embodiments of the system and method already discussed herein, the present disclosure also provides for a non-transitory storage medium containing machine readable program code. In one embodiment, this non-transitory storage medium containing machine readable program code which, when executed by a processor, causes the processor to perform the following: illuminate at least one location of a biological sample to generate at least one plurality of interacted photons, collect the plurality of interacted photons, detect the plurality of interacted photons, generate at least one Raman data set representative of the biological sample, and analyze the Raman data set to associate the biological sample with at least one disease state. In one embodiment, the storage medium, when executed by a processor, further causes the processor to pass the interacted photons through a FAST device.

EXAMPLES

FIGS. 7-17 are provided to illustrate the detection capabilities of the present disclosure for determining a disease state of a biological sample. Human blood samples collected from patients were removed from freezer storage and thawed at room temperature for approximately 1 hour. The samples were vortexed for approximately 15 seconds. 2.5 microlitres of human blood serum were dropped onto an aluminum-coated microscope slide via a micropipetter and allowed to dry for approximately 18-20 hours.

FIG. 7A is illustrative of an exemplary sample preparation utilizing a microscope slide. However, as illustrated in FIG. 7B, the present disclosure also contemplates a 96 well plate may also be used to hold samples. It is noted that duplicates of each sample (patient) were used along with both positive and negative controls.

Figure 8A:
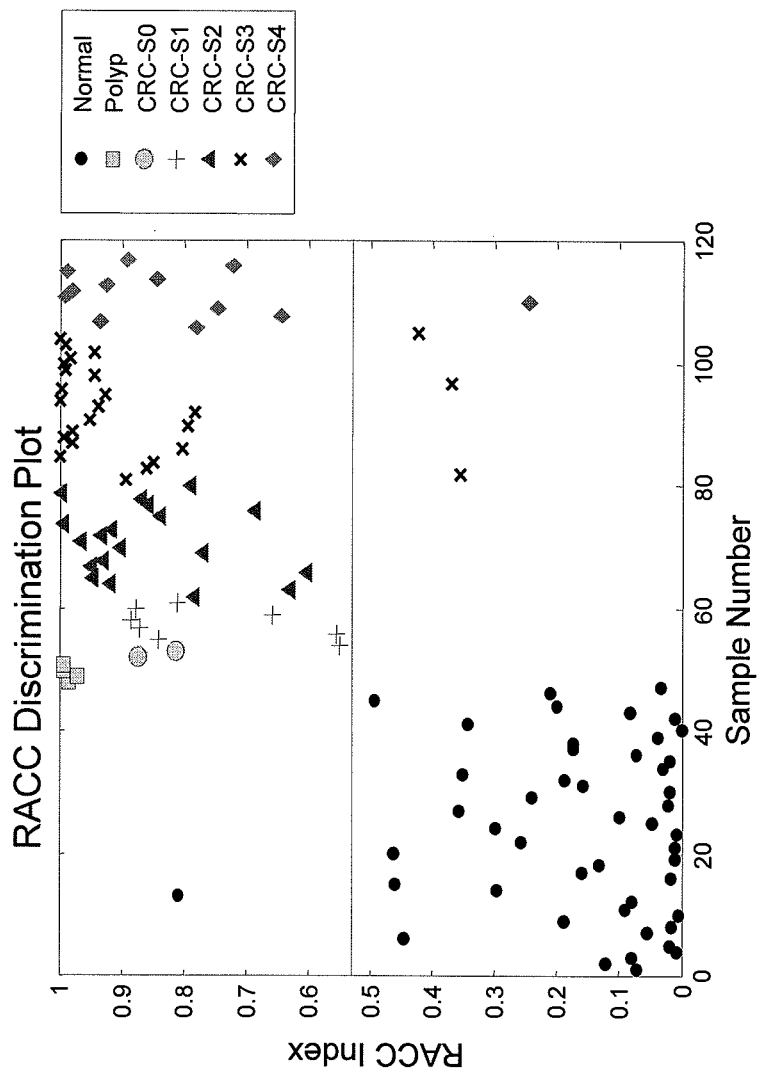
FIG. 8A is illustrative of the generation of a RACC (Raman Assay for Colorectal Cancer) Index for an exemplary set of sample data, illustrating the detection capabilities of the present disclosure for differentiating between normal, cancer, and polyp samples.
Figure 8B:
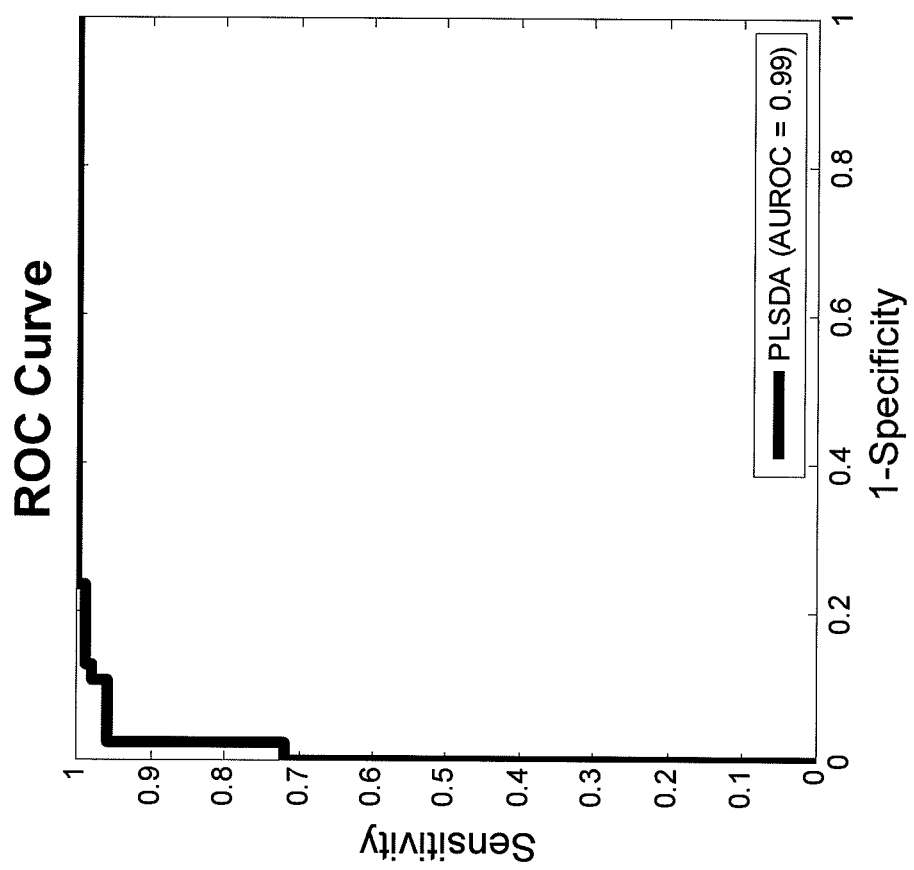
FIG. 8B is illustrative of a receiver operating characteristic (ROC) curve of an exemplary set of sample data.
Figure 8C:
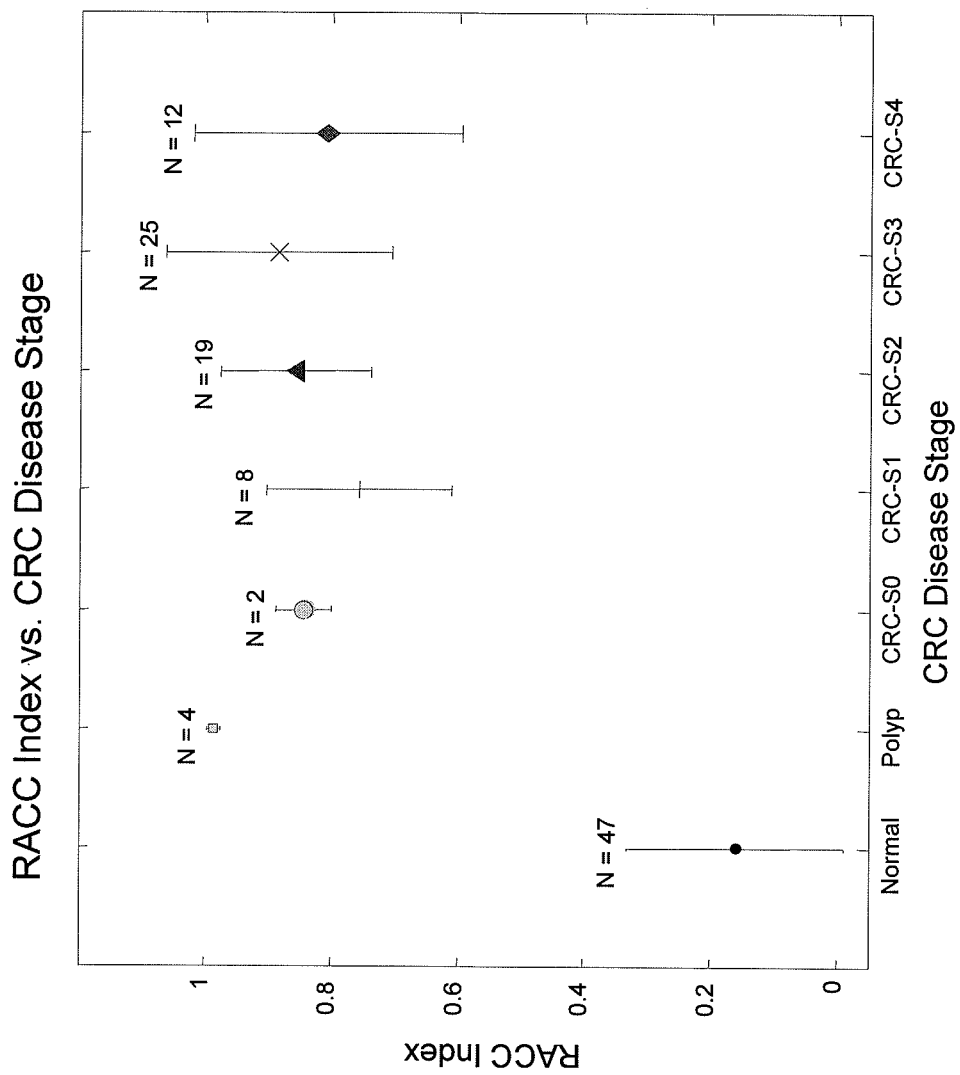
FIG. 8C is illustrative of the generation of a RACC index for an exemplary set of sample data, illustrating the detection capabilities of the present disclosure for detecting a cancer grade.

FIG. 8A is illustrative of the detection capabilities of the present disclosure. A RACC index score was generated for each sample and plotted on a RACC discrimination plot. A threshold was applied based on a corresponding ROC curve (FIG. 8B) to determining an optimal operating point. As can be seen from the plot, samples could be associated with disease stages based on their location on the plot. Samples falling below the threshold were classified as normal. Samples falling above the threshold were classified as either CRC or the presence of polyps (a potential precursor condition). For samples determined to be CRC, cancer grades can be assigned based on the RACC index. Cancer staging of the samples is illustrated in more detail in FIG. 8C, with each plot representing the mean and standard deviation for the samples belonging to each stage.

Figure 9A:
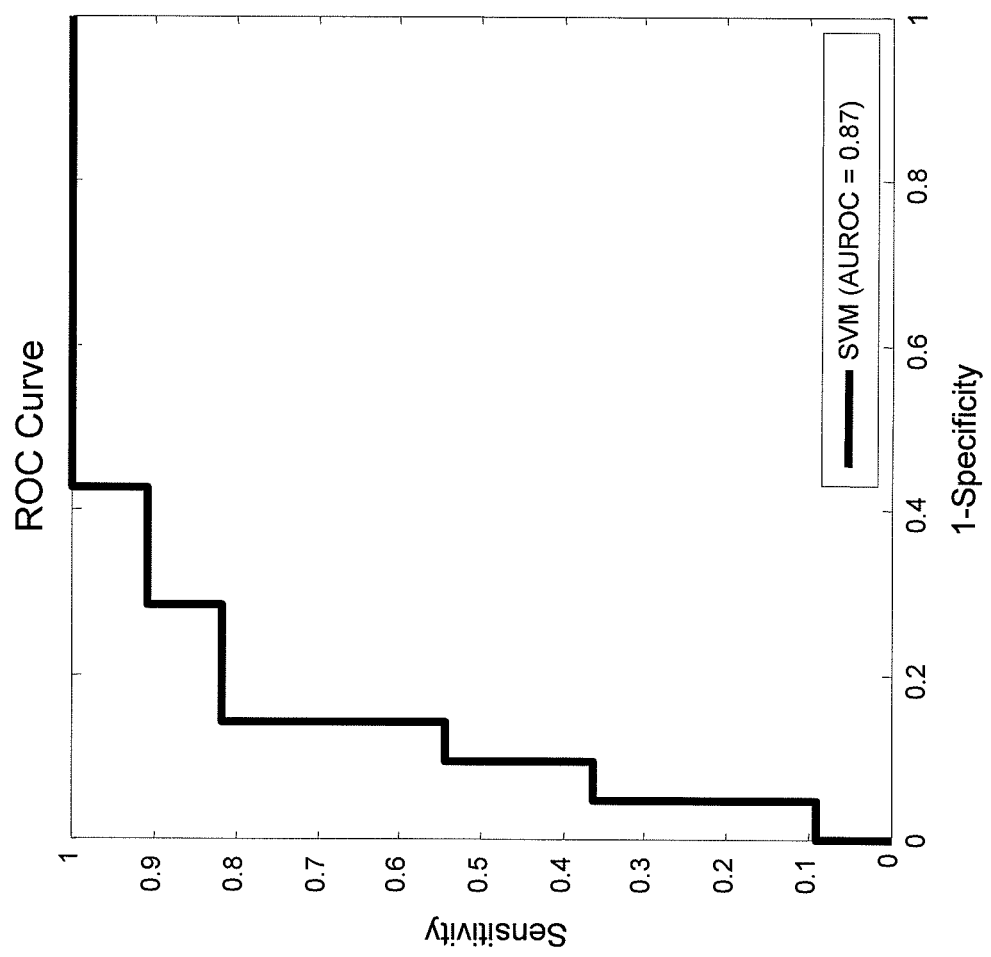
FIG. 9A is illustrative of a ROC curve of an exemplary set of sample data.
Figure 9B:
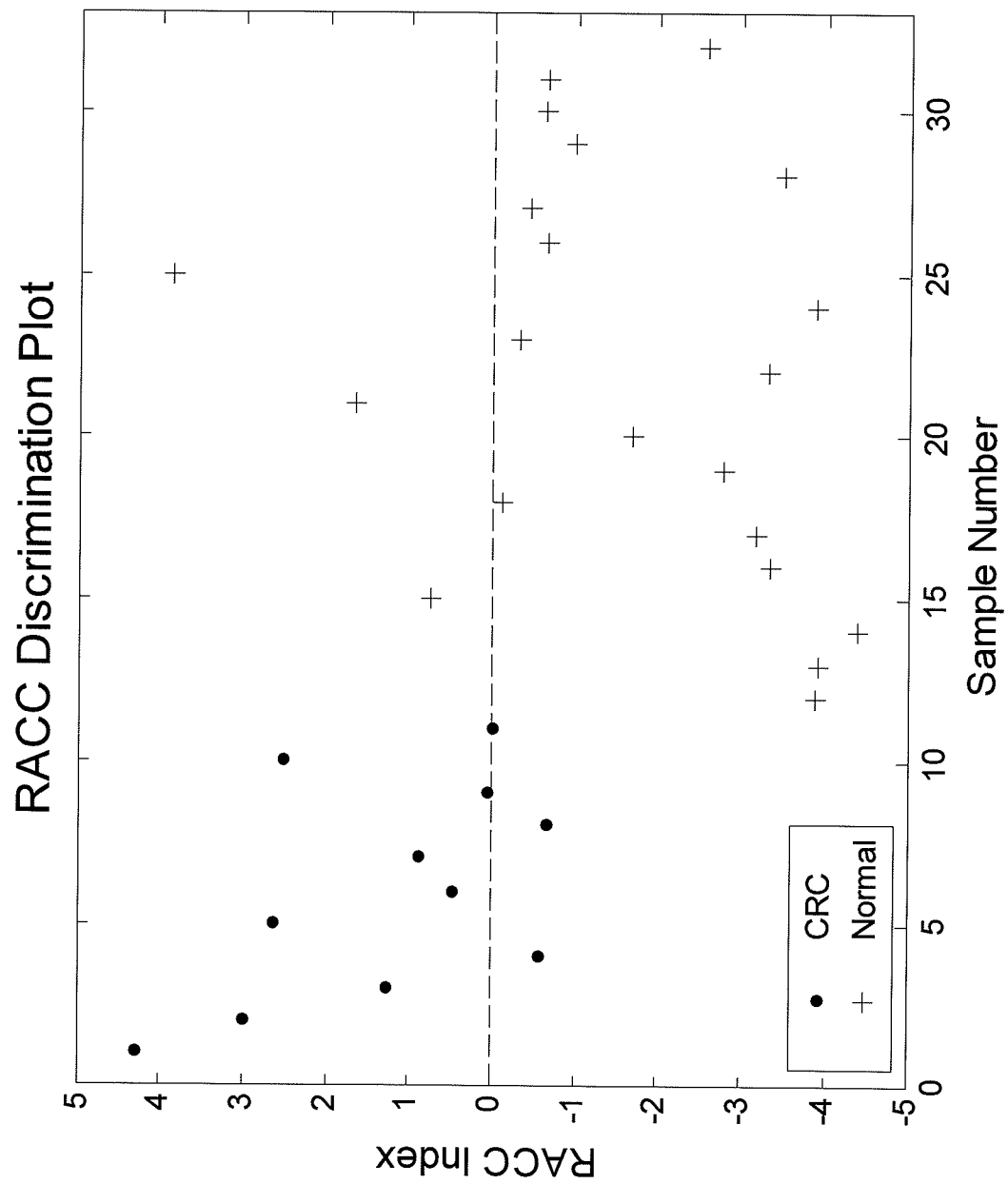
FIG. 9B is illustrative of the generation of a RACC index for an exemplary set of sample data, illustrating the detection capabilities of the present disclosure for differentiating between CRC and normal samples.

FIGS. 9A and 9B are provided to further illustrate the detection capabilities of the present disclosure and represent the results of a second study. Here, 11 CRC samples and 21 normal samples were analyzed using SVM. The ROC curve (FIG. 9A) was used to select a threshold to apply to the data as illustrated in the plot of FIG. 9B. As can be seen from FIG. 9B, CRC samples were distinguished from normal samples.

Figure 10:
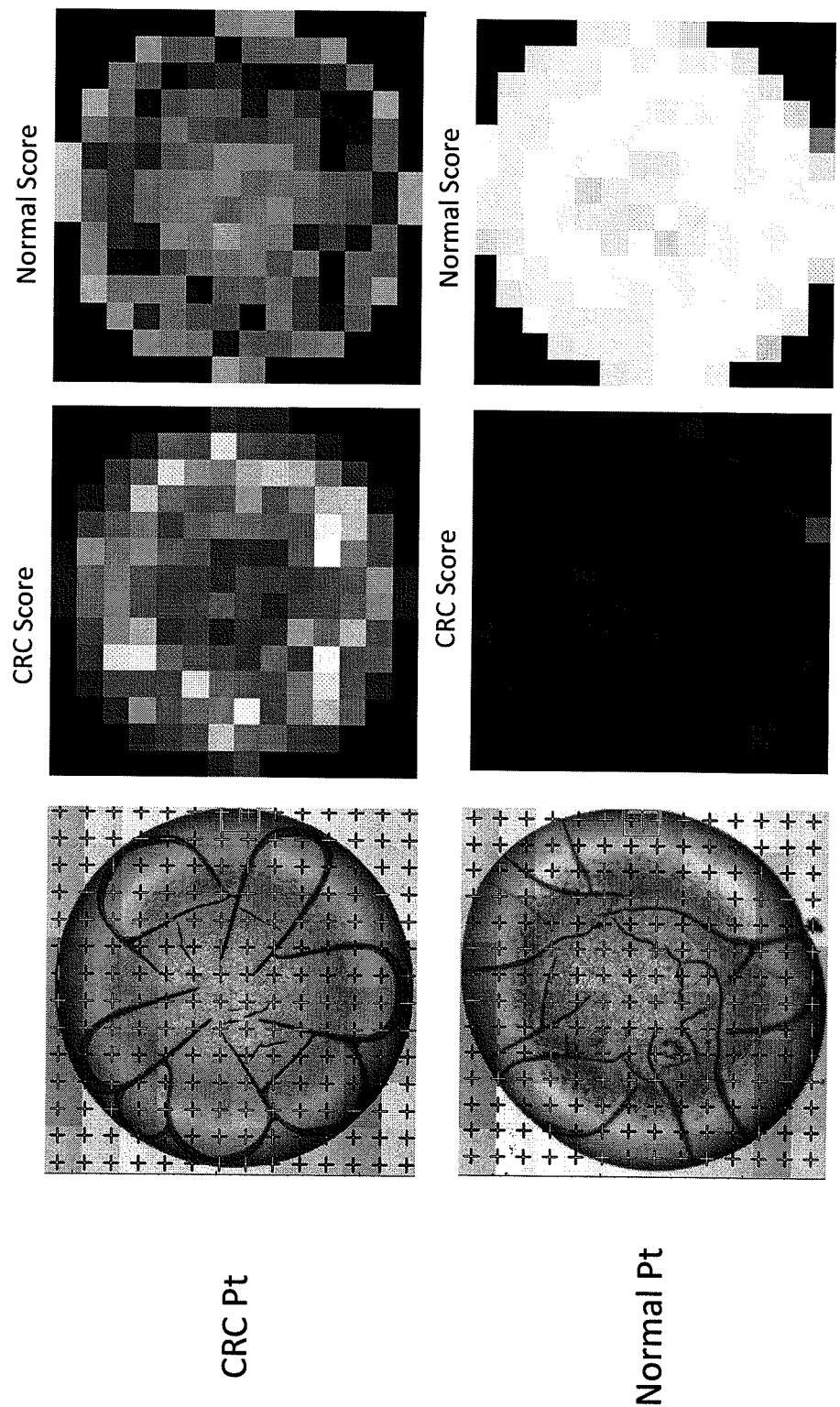
FIG. 10 is illustrative of RCI data of CRC and normal samples.

FIG. 10 illustrates high definition Raman images of samples represented by the data of FIGS. 9A and 9B, using an SVM analysis. FIG. 10 illustrates two samples from the population analyzed, one representative of a normal sample and one representative of a CRC sample. The hypercube data for each patient (sample) was analyzed against two sets of data, one corresponding to CRC and one corresponding to normal. The images illustrate a RACC index at each pixel for each sample comprising either a CRC or a normal sample. As can be seen from differences in the images, CRC and normal score images hold potential for analyzing biological samples to screen patients for cancer.

Figure 11A:
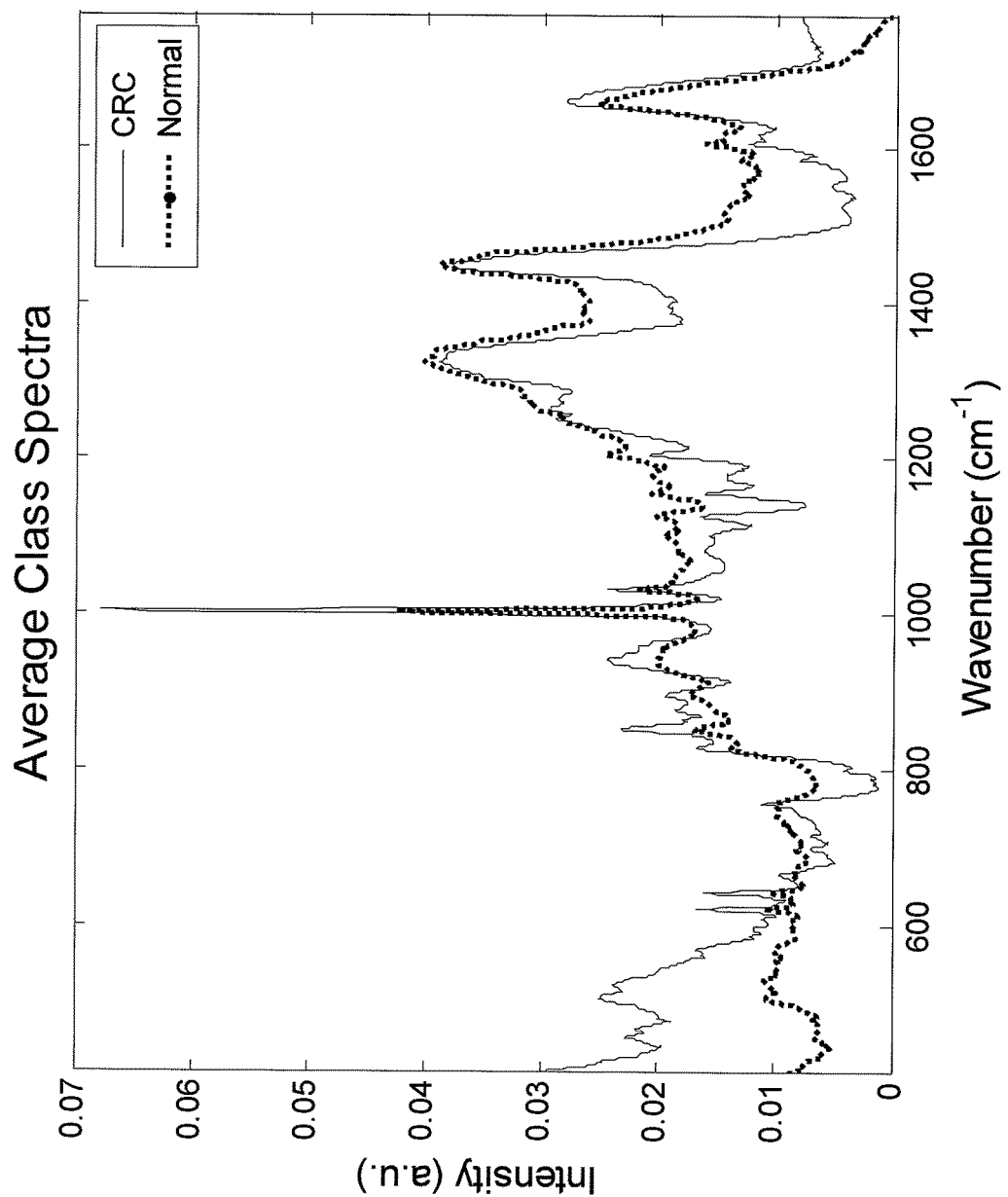
FIG. 11A is illustrative of average class spectra for the CRC and normal samples illustrated in FIG. 10.
Figure 11B:
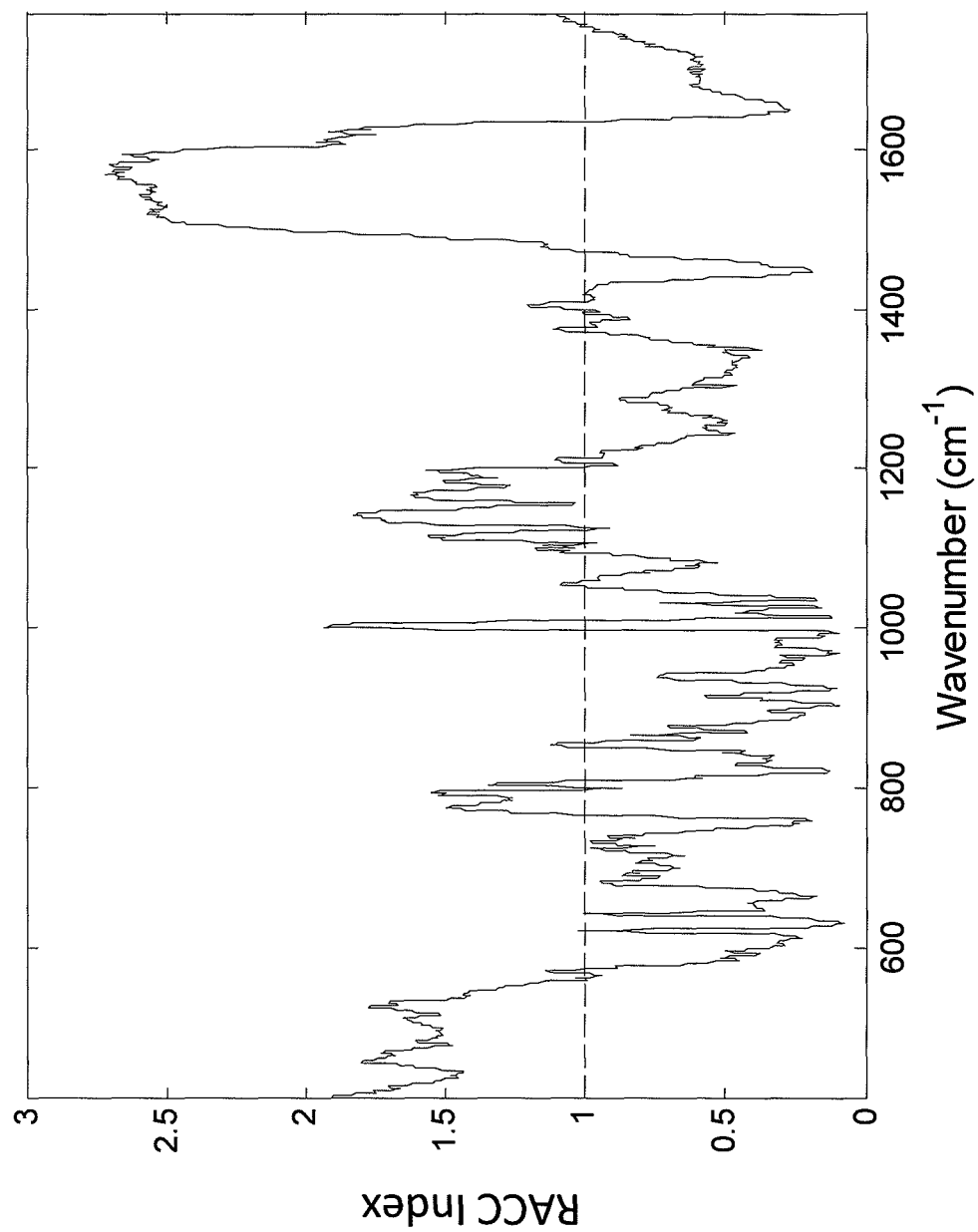
FIG. 11B is illustrative of the Variable Importance in Projection (VIP) Scores for the model differentiating CRC and normal samples illustrated in FIG. 10.

FIGS. 11A and 11B illustrate spectral data representative of the droplets of FIG. 10. FIG. 11A illustrates average class spectra for both CRC and normal samples. The differences in the spectra are clear and are indicative of the potential of Raman spectroscopy to aid in cancer screening. FIG. 11B illustrates the VIP scores for CRC samples. VIP estimates the importance of each variable in the projection used in a model and is often used for variable selection. A variable with a VIP Score close to or greater than 1 (one) can be considered important in given model. In one embodiment, spectral features that dominate the discriminating power in supervised classification models may be used to reduce the number of wavenumbers evaluated (only input the ones of importance into the chemometric/supervised learning model). Examples of spectral features may include, but are not limited to: about 502 $cm^{-1}$, about 524 $cm^{-1}$, about 540 $cm^{-1}$, about, 559 $cm^{-1}$, about 850 $cm^{-1}$, about 992 $cm^{-1}$, about 999 $cm^{-1}$, about 1010 $cm^{-1}$, about 1213 $cm^{-1}$, about 1274 $cm^{-1}$.

FIGS. 12A and 12B illustrate the potential benefits of implementing a multipoint sampling approach as contemplated by the present disclosure. FIG. 12A illustrates sampling in a grid pattern. As can be seen from the RACC index plot, CRC samples and normal samples were easily differentiated when data was generated using this sampling approach. Similarly, in FIG. 12B, CRC samples were easily differentiated from normal samples when the data was generated using a ring sampling approach. The method of the present disclosure may overcome the limitations of the prior art by enabling sampling of an outer ring of a sample (between the center of the spot and the periphery). The present embodiment can be differentiated from other techniques, such as Drop Coating Deposition Raman (DCDR). DCDR is a method that can be used to improve Raman detections in samples with low concentrations of proteins. The method comprises deposition of a protein in a solution onto a hydrophobic surface, which is prepared using a thin layer of a hydrophobic material (such as a Tienta substrate). When the solvent is removed (via drying), dried proteins in a sample may be locally enriched in an outer edge of the sample (the periphery of the sample). In contrast, the present disclosure provides for the use of samples that contain high concentrations of proteins. The method is reagentless and, unlike DCDR, does not require treatment of the samples with a solution. Also, as illustrated by FIGS. 3B and 12A, the present disclosure is not limited to sampling the periphery of a sample and holds potential for discriminating between CRC and normal samples using data obtained from the center portion of a sample.

FIG. 12C is provided to illustrate statistical data regarding the sampling approaches of FIGS. 12A and 12B. A histogram is calculated using the RACC indices from the training data, and Otsu's method splits the histogram into two parts or classes (difference between the means). The ring sampling approach improved the statistics of the model by providing a greater difference between class means and by reducing the class standard deviation.

Figure 13A:
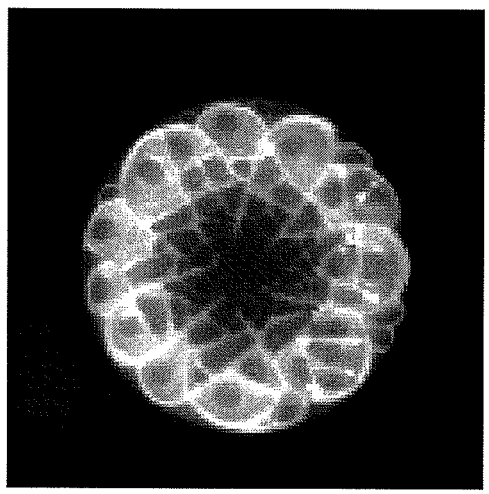
FIG. 13A is illustrative of a fluorescence chemical image of a CRC sample.
Figure 13B:
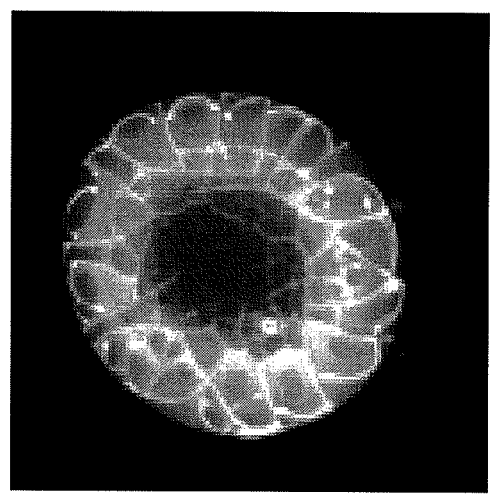
FIG. 13B is illustrative of a fluorescence chemical image of a normal sample.
Figure 14:
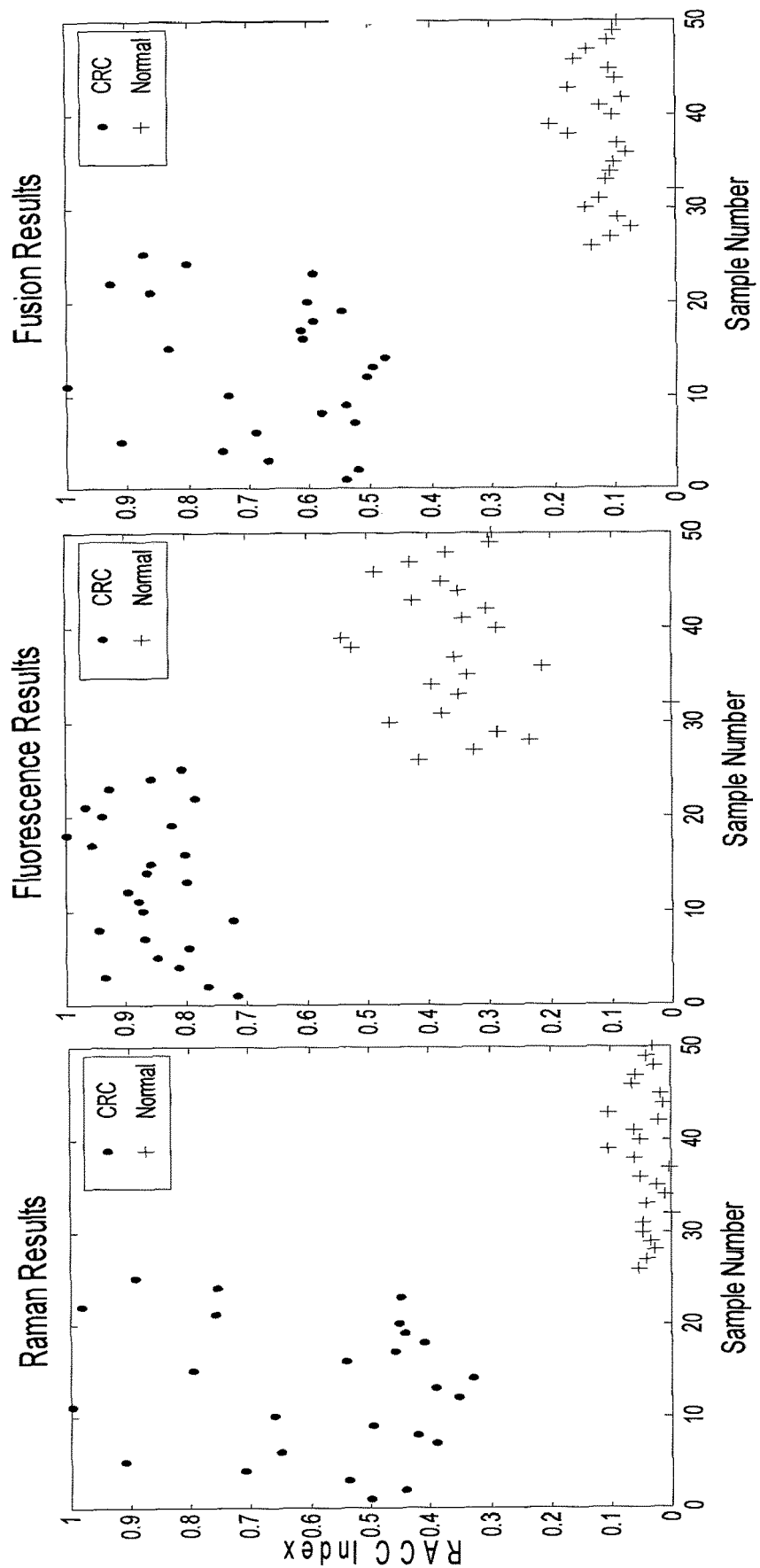
FIG. 14 is illustrative of the detection capabilities of the present discourse to differentiate between CRC and normal samples using data fusion.

FIGS. 13A-13B and FIG. 14 are provided to illustrate the capabilities of the present disclosure to fuse data from multiple modalities. FIGS. 13A and 13B represent fluorescence images of a CRC patient and a normal patient, respectively. In one embodiment, RACC indices resulting from SVM applied to Raman spectra for a patient were fused with RACC indices calculated from SVM applied to fluorescence spectra for the same patient. Fusion was done using IWBF. The fused results improved the RACC index distribution. In this example, fusion took advantage of the small distribution of the RACC indices for CRC samples in the fluorescence data and improved the distribution of the RACC index for CRC in the Raman data. Similarly for the normal samples, fusion improved the RACC index distribution of the fluorescence samples and capitalized on the tight distribution of RACC indices in the Raman data. The results of data fusion are illustrated in FIG. 14. As can be seen from the FIGS, data from multiple spectroscopic modes may be used to provide a more robust data set than either modality alone.

Figure 15:
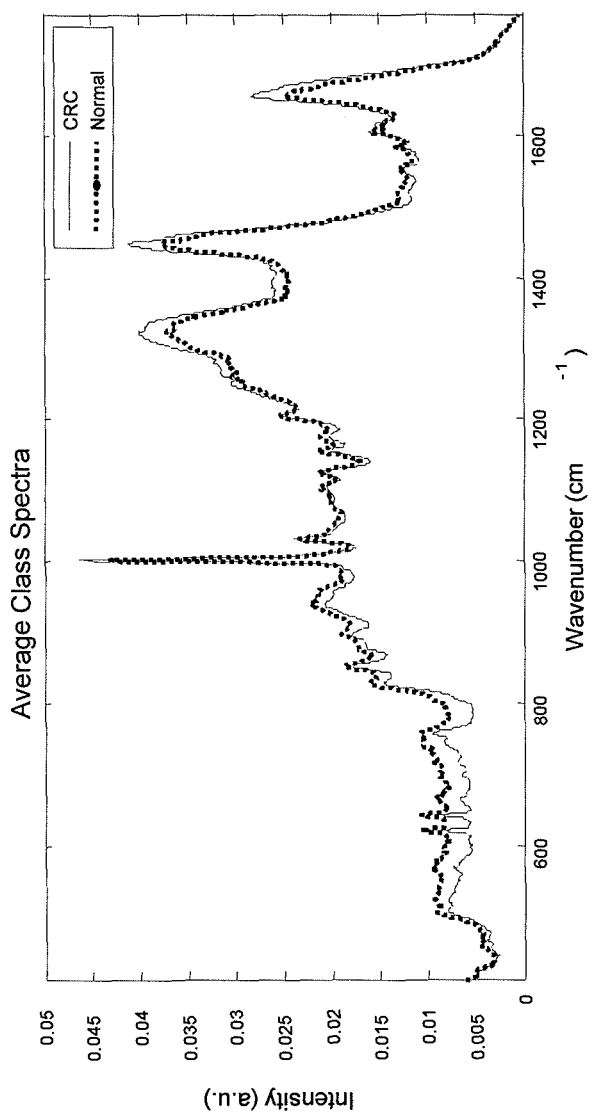
FIG. 15 is illustrative of the ability of the present disclosure to analyze a variety of spectral features including those associated with protein conformation.

As discussed herein, the present disclosure contemplates that in one embodiment, a manifold of spectral features may be evaluated to determine a disease state of a biological sample. FIGS. 15-18 are provided to further illustrate an embodiment of the present disclosure wherein protein conformation is assessed as at least a primary factor in determining whether a sample comprises CRC. For example, FIG. 15 illustrates the average Raman spectra associated with CRC and Normal blood serum samples for exemplary data. The Raman spectra exhibit scattering from blood serum proteins as the dominant molecular moieties. Raman spectroscopy has demonstrated capability for the detection of protein conformation, and the basis of discrimination between CRC and normal serum samples arises chiefly from changes in the conformation of one or more high abundance serum proteins. FIG. 16 summarizes several Raman spectral features observable in blood serum Raman spectra that indicate blood serum protein conformation. Analysis of these spectral features, where the identified wavenumber ($cm^{-1}$) position corresponds to the approximate centroid of the spectral feature, suggests that CRC blood serum samples contain increased Random Coil protein conformation relative to Normal blood serum samples. Specifically, the CRC Raman spectra evidence an increase in the shoulder band centered at 1660.6 $cm^{-1}$, which can be measured as an increase in the center of mass (COM) of the Amide I peak and is an indication of increased Random Coil protein conformation.

Figure 17:
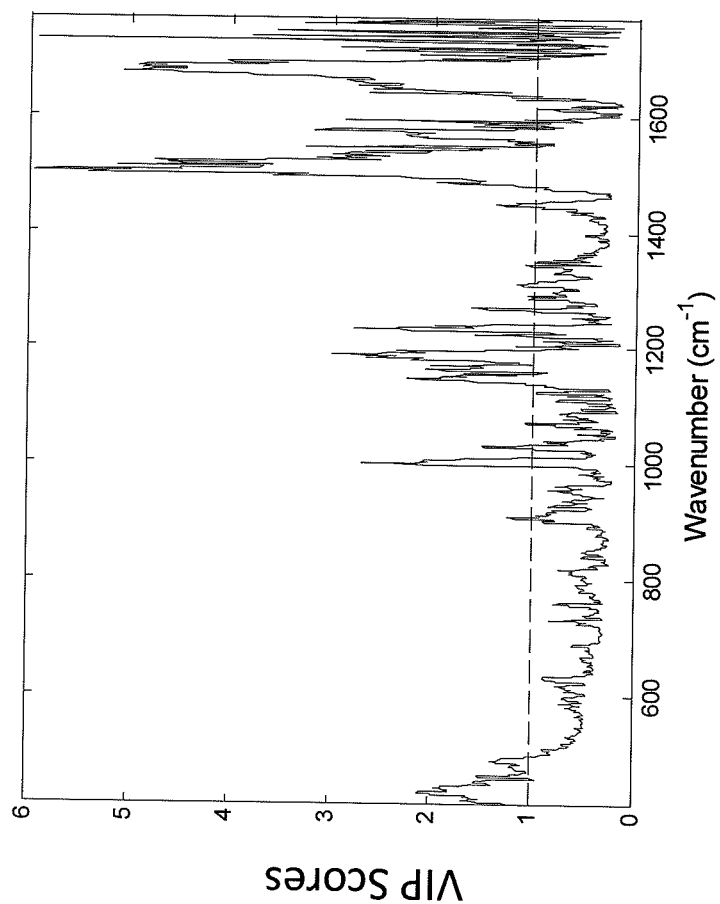
FIG. 17 is illustrative of VIP scores for a model differentiating CRC and normal samples.

In comparison, the Normal Raman spectra evidence a reduced COM to 1660.3 $cm^{-1}$, which indicates more ordered, $\alpha$-helix, protein conformation. Other observable changes that indicate the general trend of higher degree of Random Coil protein conformation in CRC spectra and higher degree of $\alpha$-helix protein conformation in Normal spectra include: (1) increase at 1263 $cm^{-1}$ (Amide III spectral feature) in Normal spectra; (2) increase at 941 $cm^{-1}$ (C—C Stretch of Polypeptide Backbone spectral feature) in Normal spectra; and (3) increase in 857/827 $cm^{-1}$ doublet ratio (Tyrosine Fermi Resonance Doublet) in CRC spectra. FIG. 17 illustrates the VIP Scores generated for these samples.

Figure 18A:
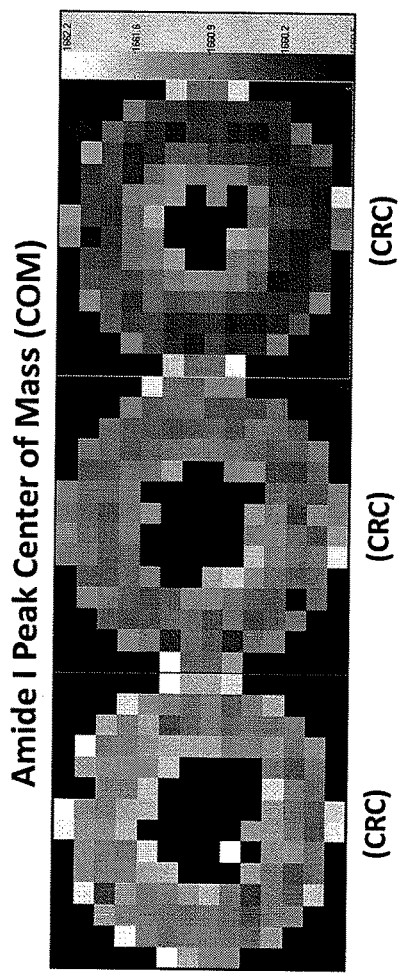
FIG. 18 A is illustrative of RCI data relating to amide 1 peak center of mass (COM).
FIG. 18B is illustrative of spectral data indicating a random coil conformation.
Figure 18B:
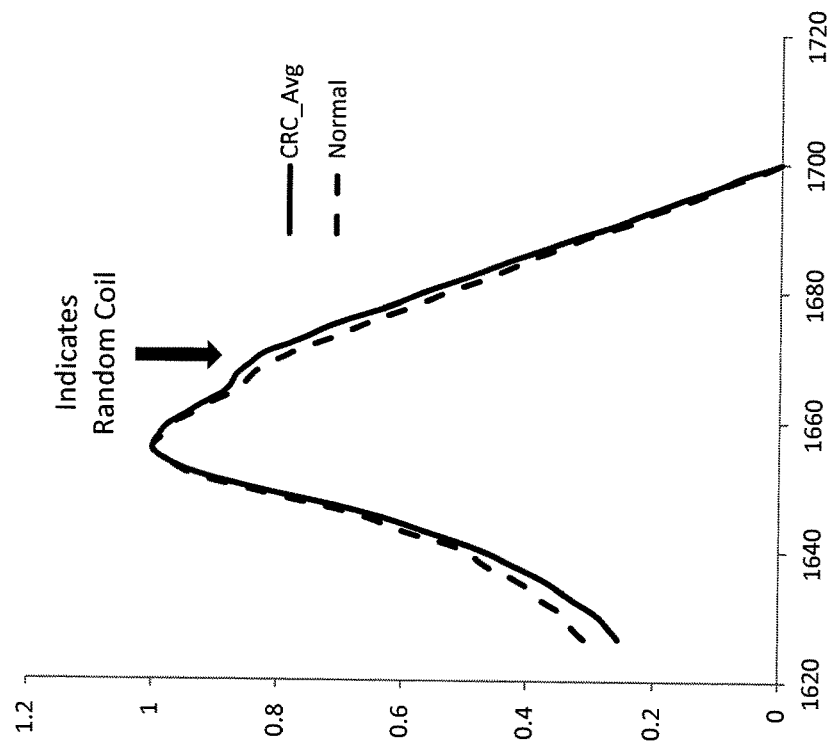

FIG. 18A is illustrative of RCI data relating to amide 1 peak COM. Amide 1 vibration is a result of primarily (about 80%) C=O stretching mode, with minor contributions from C—N stretching and C$\alpha$-CN deformation. It is also sensitive to protein secondary structure. FIG. 18B is illustrative of spectral data from these samples that illustrate differences between the CRC spectrum and the normal spectrum. This difference may indicate a random coil conformation and be used to distinguish between CRC samples and normal samples.

While the disclosure has been described in detail in reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A method comprising:
    illuminating a biological sample that is a body fluid droplet that has not been treated with a solution or a reagent to generate a plurality of interacted photons;
    collecting a first portion of the plurality of interacted photons to generate a plurality of collected photons;
    passing the collected photons through a fiber array spectral translator to generate a plurality of photons comprising a plurality of wavelengths, wherein the fiber array spectral translator comprises a two dimensional array of optical fibers drawn into a one dimensional fiber stack, the fiber array spectral translator configured to receive the plurality of collected photons at the two-dimensional array of fibers and convert the plurality of collected photons into a linear arrangement;
    detecting the linear arrangement of the plurality of collected photons exiting the fiber array spectral translator to generate a Raman data set; and
    analyzing the Raman data set to identify a disease state by sampling along an outer ring of the biological sample that is between the center of the biological sample and the periphery of the biological sample.

2. The method of claim 1, wherein the body fluid droplet comprises one or more of urine, saliva, sputum, feces, blood, serum, plasma, mucus, pus, semen, fluid expressed from a wound, lavage, cerebrospinal fluid, or vaginal fluid.

3. The method of claim 2, wherein the body fluid droplet is selected from the group consisting of serum and plasma.

4. The method of claim 1, wherein the illuminating comprises illuminating a plurality of points of the biological sample.

5. The method of claim 4, wherein illuminating the plurality of points comprises illuminating the plurality of points by structured illumination.

6. The method of claim 4, wherein the plurality of points comprise a defined geometric relationship.

7. The method of claim 4, wherein the plurality of points comprise a line.

8. The method of claim 1, wherein the illuminating comprises wide-field illumination.

9. The method of claim 1, wherein the disease state comprises one or more of a cancer type and a polyp.

10. The method of claim 1, wherein the disease state comprises a cancer stage.

11. The method of claim 1, wherein the disease state comprises colorectal cancer.

12. The method of claim 1, wherein the disease state comprises one or more of an immune response and an inflammatory response.

13. The method of claim 1, wherein the illuminating comprises illuminating the biological sample with an infrared laser.

14. The method of claim 13, wherein the infrared laser comprises a laser having a wavelength of 785 nm.

15. The method of claim 1, wherein the Raman data set comprises a Raman spectrum.

16. The method of claim 1, wherein the Raman data set comprises a Raman chemical image.

17. The method of claim 1, wherein the analyzing comprises applying an algorithmic technique.

18. The method of claim 17, wherein the algorithmic technique comprises a chemometric technique.

19. The method of claim 18, wherein the chemometric technique further comprises one or more of a multivariate curve resolution analysis, a principal component analysis, a k means clustering analysis, a band t. entropy method analysis, an adaptive subspace detector analysis, a cosine correlation analysis, an Euclidian distance analysis, a partial least squares regression analysis, a spectral mixture resolution analysis, a spectral angle mapper metric analysis, a spectral information divergence metric analysis, a Mahalanobis distance metric analysis, and a spectral unmixing analysis.

20. The method of claim 18, wherein the chemometric technique comprises a partial least squares discriminant analysis.

21. The method of claim 17, wherein the algorithmic technique comprises support vector machines analysis.

22. The method of claim 1, further comprising collecting a second portion of the plurality of interacted photons to generate an RGB image.

23. The method of claim 22, further comprising fusing the RGB image and the Raman data set.

24. The method of claim 1, wherein analyzing the Raman data set comprises applying one or more of a whole patient outlier rejection analysis and an intra-patient outlier rejection analysis.

25. The method of claim 1, wherein analyzing the Raman data set comprises applying a calibration transfer function analysis, wherein the calibration transfer function analysis comprises applying a piece-wise linear function.

26. The method of claim 1, wherein analyzing the Raman data set comprises assessing a protein conformation.

27. The method of claim 26, wherein assessing the protein conformation by analyzing a spectral feature comprising one or more of a wavelength of approximately 1660 $cm^{-1}$, a wavelength of approximately 941 $cm^{-1}$, and a wavelength range of approximately 1230 $cm^{-1}$-1300 $cm^{-1}$.

28. The method of claim 1, wherein analyzing the Raman data set comprises associating a disordered protein conformation with a disease state comprising cancer.

29. The method of claim 2, wherein the body fluid droplet is serum.

30. A system comprising:
    an illumination source configured to illuminate a location of a biological sample that is a body fluid droplet that has not been treated with a solution or a reagent to generate a plurality of interacted photons;
    a mirror configured to direct a first portion of the plurality of interacted photons;
    a fiber array spectral translator device comprising a two dimensional array of optical fibers drawn into a one dimensional fiber stack, the fiber array spectral translator device configured to receive the first portion of the plurality of interacted photons at the two-dimensional array of fibers and convert the first portion of the plurality of interacted photons into a linear arrangement;
    a spectrometer configured to optically receive the linear arrangement of the first portion of the plurality of interacted photons from the fiber array spectral translator device and filter the first portion of the plurality of interacted photons into a plurality of filtered photons comprising a plurality of wavelengths;

a detector configured to detect the plurality of filtered photons and generate a Raman data set; and a processor configured to analyze the Raman data set by sampling along an outer ring of the biological sample that is between the center of the biological sample and the periphery of the biological sample that is a body fluid droplet to identify a disease state.

31. The system of claim 30, wherein the illumination source comprises an infrared laser.

32. The system of claim 31, wherein the infrared laser comprises a laser having a wavelength of 785 nm.

33. The system of claim 30, wherein the detector comprises one or more of a CCD detector, an ICCD detector, an InGaAs Detector, an IbSb detector, and an MCT detector.

34. The system of claim 30, further comprising an RGB detector configured to detect a second portion of the plurality of interacted photons and generate an RGB image.

35. The system of claim 34, further comprising at least one mirror configured to direct the second portion of the plurality of interacted photons to the RGB detector.

36. The system of claim 30, further comprising a stage configured for holding a biological sample.

37. The system of claim 30, further comprising at least one reference data set associated with at least one known disease state.

38. The system of claim 37, wherein the at least one known disease state comprises one or more of a cancer type and a polyp.

39. The system of claim 37, wherein the at least one disease state comprises one or more of an immune response and an inflammatory response.

40. The system of claim 30, wherein the Raman data set comprises a Raman spectrum.

41. The system of claim 30, wherein the Raman data comprises a Raman chemical image.

42. The system of claim 30, wherein the illumination source is configured to illuminate the biological sample using wide-field illumination.

43. The system of claim 30, wherein the illumination source is configured to illuminate the biological sample at a plurality of points.

44. The system of claim 43, wherein the plurality of points are linear.

45. The system of claim 30, wherein the illumination source is configured to illuminate the biological sample using structured illumination.

46. The system of claim 30, wherein the processor is configured to analyze the Raman data set by applying an algorithmic technique.

47. The system of claim 46, wherein the analyzing comprises comparing the Raman data set to at least one reference data set.

48. The system of claim 30, wherein the body fluid droplet is serum.

49. A non-transitory storage medium containing machine readable program code, which, when executed by a processor, causes the processor to:

cause an illumination source to illuminate a location of a biological sample that is a body fluid droplet that has not been treated with a solution or a reagent to generate a plurality of interacted photons;

cause a collection device to collect the plurality of interacted photons and generate a plurality of collected photons;

cause a fiber array spectral translator device to receive the plurality of collected photons at a two dimensional array of optical fibers and convert the plurality of collected photons into a linear arrangement at a one-dimensional fiber stack;

cause a detector to detect the linear arrangement of the plurality of collected photons and generate a Raman data set; and analyze the Raman data set to identify a disease state, wherein the analyzing of the Raman data set is performed by sampling along an outer ring of the biological sample that is between the center of the biological sample and the periphery of the biological sample.

50. The non-transitory storage medium containing machine readable code of claim 49, wherein the body fluid droplet is serum.

* * * * *